(12) United States Patent
Kinch et al.

(10) Patent No.: US 8,591,887 B2
(45) Date of Patent: *Nov. 26, 2013

(54) EPHA2 AS A THERAPEUTIC TARGET FOR CANCER

(75) Inventors: Michael S. Kinch, Laytonsville, MD (US); Nicole D. Zantek, Edina, MN (US); Patrick W. Hein, West Lafayette, IN (US)

(73) Assignee: Purdue Research Foundation, West Lafayette (IN)

( * ) Notice: Subject to any disclaimer, the term of this patent is extended or adjusted under 35 U.S.C. 154(b) by 385 days.

This patent is subject to a terminal disclaimer.

(21) Appl. No.: 12/655,782

(22) Filed: Jan. 7, 2010

(65) Prior Publication Data

US 2011/0150898 A1   Jun. 23, 2011

Related U.S. Application Data

(63) Continuation of application No. 11/063,101, filed on Feb. 22, 2005, now abandoned, which is a continuation of application No. 09/640,935, filed on Aug. 17, 2000, now Pat. No. 6,927,203.

(60) Provisional application No. 60/149,258, filed on Aug. 17, 1999.

(51) Int. Cl.
*A61K 39/395* (2006.01)
*A61K 38/00* (2006.01)

(52) U.S. Cl.
USPC ........................ 424/130.1; 424/141.1; 514/1.1

(58) Field of Classification Search
None
See application file for complete search history.

(56) References Cited

U.S. PATENT DOCUMENTS

| | | | |
|---|---|---|---|
| 4,472,371 A | 9/1984 | Burchiel et al. | |
| 4,704,692 A | 11/1987 | Ladner | |
| 4,816,567 A | 3/1989 | Cabilly et al. | |
| 5,001,225 A | 3/1991 | Taylor | |
| 5,447,936 A | 9/1995 | Hausheer et al. | |
| 5,457,048 A | 10/1995 | Pasquale et al. | |
| 5,514,554 A | 5/1996 | Bacus | |
| 5,585,089 A | 12/1996 | Queen et al. | |
| 5,635,177 A | 6/1997 | Bennett et al. | |
| 5,770,195 A | 6/1998 | Hudziak et al. | |
| 5,795,734 A | 8/1998 | Flanagan et al. | |
| 5,811,098 A | 9/1998 | Plowman et al. | |
| 5,824,303 A | 10/1998 | Bartley et al. | |
| 5,872,223 A | 2/1999 | Uckun | |
| 5,876,949 A | 3/1999 | Dreyfuss et al. | |
| 5,981,245 A | 11/1999 | Fox et al. | |
| 6,057,105 A | 5/2000 | Hoon et al. | |
| 6,174,670 B1 | 1/2001 | Wittwer et al. | |
| 6,927,203 B1 | 8/2005 | Kinch et al. | |
| 7,033,594 B2 | 4/2006 | Low et al. | |
| 7,101,976 B1 | 9/2006 | Kilpatrick et al. | |
| 7,192,698 B1 | 3/2007 | Kinch et al. | |
| 7,402,298 B1 | 7/2008 | Kinch et al. | |
| 7,662,770 B2 | 2/2010 | Kinch | |
| 7,776,327 B2 | 8/2010 | Kinch | |
| 7,776,328 B2 | 8/2010 | Mather | |
| 2001/0031252 A1 | 10/2001 | Low et al. | |
| 2001/0031262 A1 | 10/2001 | Caplan et al. | |
| 2004/0028685 A1 | 2/2004 | Kinch et al. | |
| 2004/0091486 A1 | 5/2004 | Kinch et al. | |
| 2005/0152899 A1 | 7/2005 | Kinch et al. | |
| 2005/0169931 A1 | 8/2005 | Kinch et al. | |
| 2006/0088541 A1 | 4/2006 | Kinch et al. | |
| 2007/0086943 A1 | 4/2007 | Kinch et al. | |
| 2007/0134254 A1 | 6/2007 | Kinch et al. | |
| 2007/0161064 A1 | 7/2007 | Kinch et al. | |
| 2007/0166314 A1 | 7/2007 | Kinch et al. | |
| 2009/0220527 A1 | 9/2009 | Damschroeder et al. | |
| 2010/0143345 A1 | 6/2010 | Kinch et al. | |
| 2010/0278838 A1 | 11/2010 | Kinch et al. | |
| 2010/0298545 A1 | 11/2010 | Kinch | |

FOREIGN PATENT DOCUMENTS

| | | |
|---|---|---|
| EP | 0 599 274 A1 | 6/1994 |
| EP | 1 242 060 B1 | 5/2006 |
| JP | 07-132084 | 5/1995 |
| JP | 10-500858 | 1/1998 |
| WO | WO 93/00425 A1 | 1/1993 |
| WO | WO 94/04679 A1 | 3/1994 |
| WO | WO 94/11020 A1 | 5/1994 |
| WO | WO 94/29348 A2 | 12/1994 |
| WO | WO 95/15375 A1 | 6/1995 |
| WO | WO 95/33772 A1 | 12/1995 |
| WO | WO 96/36713 A2 | 11/1996 |
| WO | WO 96/36713 A3 | 5/1997 |
| WO | WO 97/15587 A1 | 5/1997 |
| WO | WO 98/43960 A1 | 10/1998 |

(Continued)

OTHER PUBLICATIONS

Jain, "Barriers to drug delivery in solid tumors", Sci Am. 171(1): 58-65, 1994.*

(Continued)

*Primary Examiner* — Hong Sang
(74) *Attorney, Agent, or Firm* — Mueting Raasch & Gebhardt, P.A.

(57) ABSTRACT

The present invention is directed to compounds and methods for the treatment of metastatic disease. The compounds of this invention have specificity for EphA2, an epithelial cell tyrosine kinase that is overexpressed in metastatic tumor cells. The compounds used in accordance with this invention may be provided in a pharmaceutical composition for treatment of metastatic disease.

6 Claims, 2 Drawing Sheets

(56) References Cited

FOREIGN PATENT DOCUMENTS

| WO | WO 00/30673 A1 | 6/2000 |
|---|---|---|
| WO | WO 00/37500 A1 | 6/2000 |
| WO | WO 01/12172 A1 | 2/2001 |
| WO | WO 01/12840 A2 | 2/2001 |
| WO | WO 01/12840 A3 | 5/2001 |
| WO | WO 01/47892 A1 | 7/2001 |
| WO | WO 02/30465 A2 | 4/2002 |
| WO | WO 02/30465 A3 | 3/2003 |
| WO | WO 03/094859 A2 | 11/2003 |
| WO | WO 03/099313 A1 | 12/2003 |
| WO | WO 2004/014292 A2 | 2/2004 |
| WO | WO 03/094859 A3 | 2/2005 |
| WO | WO 2005/051307 A2 | 6/2005 |
| WO | WO 2005/056766 A2 | 6/2005 |
| WO | WO 2004/014292 A3 | 2/2006 |
| WO | WO 2005/051307 A3 | 9/2006 |
| WO | WO 2005/056766 A3 | 1/2008 |

OTHER PUBLICATIONS

Gura, "Systems for identifying new drugs are often faulty", Science 278 (5340), 1041-1042, 1997.*
MSNBC News Services, "Mixed results on new cancer drug", Nov. 2000, total pp. 4.*
Freshney, Culture of Animal Cells, A Manual of Basic Technique, Alan R. Liss, Inc., 1983, New York, pp. 3-4.*
Dermer, Bio/Technology, 1994, 12:320.*
Zips et al., In Vivo, 2005, 19:1-7.*
"2,2'-azinobis(3-ethylbenzothiazoline-6-sulfonic acid) (ABTS) Substrate Solution" MSDS. Pierce Biotechnology: Rockford, Illinois. Available online [retrieved Mar. 7, 2008]. Retrieved from the Internet: <http://www.piercenet.com/files/EN0795.pdf>; 6 pages.
Aasheim et al., "A splice variant of human ephrin-A4 encodes a soluble molecule that is secreted by activated human B lymphocytes." 2000 Blood. 95(1):221-30.
Abrahmsen et al., "Engineering Subtilisin and Its Substrates for Efficient Ligation of Peptide Bonds in Aqueous Solution." 1991 Biochemistry, 30:4151-4159.
Agre et al., "The human tumor cloning assay in cancer drug development." 1983 Investigational New Drugs 1:033-045.
Alves et al., "EphA2 as Target of Anticancer Immunotherapy: Identification of HLA-A*0201-Restricted Epitopes," Dec. 1, 2003 Cancer Research 63:8476-8480.
Andres et al., "Expression of two novel eph-related receptor protein tyrosine kinases in mammary gland development and carcinogenesis." 1994 Oncogene 9:1461-1467.
Angrist et al., "Chromosomal Localization of the Mouse Src-like Adapter Protein (Slap) Gene and Its putative Human Homolog SLA." 1995 Genomics 30:623-625.
Bae et al., "Molecular and cellular analysis of basement membrane invasion by human breast cancer cells in Matrigel-based in vitro assays." 1993 Breast Cancer Res. Treat. 24:241-255.
Baggiolini et al., "Interleukin-8, a chemotactic and inflammatory cytokine." 1992 FEBS Lett., 307(1):97-101.
Baggliolini et al., "Interleukin-8 and the Chemokine Family." 1995 Int. J. Immunopharmae 17(2):103-108.
Bartley et al., "B61 is a ligand for the ECK receptor protein-tyrosine kinase." 1994 Nature 368:558-560.
Baselga et al., "Recombinant Humanized Anti-HER2 Antibody (Herceptin™) Enhances the Antitumor Activity of Paclitaxel and Doxorubicin against HER2/neu Overexpressing Human Breast Cancer Xenografts." 1998 Cancer Res. 58:2825-2831.
Becker et al., "Characterization of the SEK-1 receptor tyrosine kinase" 1995 FEBS Letters 368(2):353-357.
Behrens et al., "Cell-cell adhesion in invasion and metastasis of carcinomas." 1994 Cancer Treat. Res. 71:251-266.
Biervert et al., "Semiquantitative expression analysis of ephrine-receptor tyrosine kinase mRNA's in a rat model of traumatic brain injury." 2001 Neurosci Lett. 315(1-2):25-8.
Birchmeier, "E-cadherin as a tumor (invasion) suppressor gene." 1995 Bioessays 17:97-99.
Blanco et al., "Expression of EphA receptors and ligands during chick cerebellar development." 2002 Mech. Dev. 114(1-2):225-9.
Bodanszky et al., Ed., Principles of Peptide Synthesis, Springer-Verlag Inc., NY, 1993, Cover pg., Publication pg., and Table of Contents.
Boerner et al., "Production of antigen-Specific Human Monoclonal Antibodies from in vitro-primed Human Splenocytes." 1991 J. Immunol. 147(1):86-95.
Bohme et al., "PCR mediated detection of a new human receptor-tyrosine-kinase, HEK 2." 1993 Oncogene. 8(10):2857-62.
Bovenkamp et al., "Degenerate PCR-based cloning method for Eph receptors and analysis of their expression in the developing murine central nervous system and vasculature." 2001 DNA Cell Biol. 20(4):203-13.
Bowie et al., "Deciphering the Message in Protein Sequences: Tolerance to Amino Acid Substitutions." 1990 Science 247:1306-1310.
Brady-Kalnay et al., "Dynamic Interaction of PTPμ with Multiple Cadherins In Vivo." 1998 J. Cell Biol. 141:287-296.
Brantley et al., "Soluble Eph A receptors inhibit tumor angiogenesis and progression in vivo." 2002 Oncogene. 21(46):7011-26.
Brodeur et al., "Mouse-Human Myeloma Partners for the Production of Heterohybridomas, Monoclonal Antibody Production." 1987 Techniques and Application 51-63.
Bruggemann et al., "Designer mice: the production of human antibody repertoires in transgenic animals." 1993 Year Immunol. 7:33-40.
Burgess et al., "Possible Dissociation of the Heparin-binding Mitogenic Activities of Heparin-binding (Acidic Fibroblast) Growth Factor-1 from Its Receptor-binding Activities by Site-directed Mutgensis of a Single Lysine Residue." 1990 J. Cell Biology 111:2129-2138.
Burridge et al., "Focal adhesions: transmembrane junctions between the extracellular matrix and the cytoskeleton," 1988 Annu. Rev. Cell Dev. Biol. 4:487-525.
Burridge et al., "Focal adhesions, contractility, and signaling." 1996 Annu. Rev. Cell Dev. Biol. 12:463-518.
Bynum et al., "Development of Class-Switched, Affinity-Matured Monoclonal Antibodies Following a 7-Day Immunization Schedule." 1999 Hybridoma 18:407-411.
Campbell, Monoclonal Antibody Technology, 1985, pp. 1-32.
Cance et al., "Protein kinases in human breast cancer." 1995 Breast Cancer Research and Treatment, 35:105-114.
Carles-Kinch, "Antibody Targeting of the EphA2 Tyrosine Kinase Inhibits Malignant Cell Behavior." 2002 Cancer Research 62:2840-2847.
Carter et al., "Humanization of an anti-p185$^{HER2}$ antibody for human cancer therapy." 1992 Proc. Natl. Acad. Sci. USA 89:4285-4289.
Carter et al., "EphrinA 1-induced cytoskeletal re-organization requires FAK and p130(cas)." 2002 Nat Cell Biol. 4(8):565-73.
Chen et al., "Integrin-mediated cell adhesion activates mitogen-activated protein kinases." 1994 J. Biol. Chem. 269:26002-26005.
Chen et al., "Germ-line inactivation of the murine Eck receptor tyrosine kinase by gene trap retroviral insertion." 1996 Oncogene 12(5):979-88.
Chen et al., "An enhancer element in the EphA2 (Eck) gene sufficient for rhombomere-specific expression is activated by HOXA1 and HOXB1 homeobox proteins." 1998 J Biol Chem. 273(38):24670-5.
Cheng et al., "Blockade of EphA Receptor Tyrosine Kinase Activation Inhibits Vascular Endothelial Cell Growth Factor-Induced Angiogenesis." 2002 Mol Cancer Res. 1(1):2-11.
Chothia et al., "Canonical Structures for the Hypervariable Regions of Immunoglobulins." 1987 J. Mol. Biol. 196:901-917.
Clark et al., "Aberrant function of the Ras signal transduction pathway in human breast cancer." 1995 Breast Cancer Res. Treat. 35(1):133-144.
Clark, Protein Engineering of Antibody Molecules for Prophylactic and Therapeutic Applications in Man, Academic Titles, Nottingham, England, 1993, title page, copyright page, pp. 4-5.
Clark et al., "Overexpression of the Ras-related TC21/R-Ras2 protein may contribute to the development of human breast cancers." 1996 Oncogene, 12:169-176.

(56) References Cited

OTHER PUBLICATIONS

Clark et al., "The Ras-related protein Fheb is farnesylated and antagonizes Ras signaling and transformation." 1997 *J. Biol. Chem.* 272:10608-10615.
Clark-Lewis et al., "Chemical Synthesis, Purification, and Characterization of Two Inflammatory Proteins, Neutrophil Activating Peptide 1 (Interleukin-8) and Neutrophil Activating Peptide 2." 1991 *Biochemistry* 30:3128-3135.
Clark-Lewis et al., "Structural Requirements for Interleukin-8 Function Identified by Design of Analogs and CXC Chemokine Hybrids." 1994 *J. Biol. Chem*, 269:16075-16081.
Coffman et al., "Differential EphA2 Epitope Display on Normal versus Malignant Cells," 2003 *Cancer Research* 63:7907-7912.
Cole et al., Monoclonal Antibodies and Cancer Therapy, Alan R. Liss, ed.; 1985, p. 77.
Connor et al., "Expression and tyrosine phosphorylation of Eph receptors suggest multiple mechanisms in patterning of the visual system." 1998 *Dev Biol.* 193(1):21-35.
Curti, "Physical barriers to drug delivery in tumors." 1993 *Critical Reviews in Oncology/Hematology* 14:29-39.
Dall'Acqua et al., "Antibody humanization by framework shuffling," 2005 *Methods* 36:43-60.
D'Amico, "Predicting the Sites of Metastasis Form Lung Cancer Using Molecular Biologic Markets." 2001 *Ann. Thorac. Surg.* 72:1144-8.
Damschroder et al., "Framework shuffling of antibodies to reduce immunogenicity and manipulate functional and biophysical properties," 2007 *Molecular Immunology* 44:3049-3060.
Davis et al., "Ligands for EPH-related receptor tyrosine kinases that require membrane attachment or clustering for activity." 1994 *Science* 266:816-819.
Dawson et al., "Synthesis of Proteins by Native Chemical Ligation." 1994 *Science* 266:776-779.
deLisle et al., *Techniques in Protein Chemistry IV*, Academic Press, New York, 1992; pp. 257-267.
Dermer, "Another Anniversary for the War on Cancer." 1994 *Bio/Technology* 12:320.
DeVita, Jr., "Principles of Cancer Management: Chemotherapy", *Cancer: Principles and Practice of Oncology, Fifth Edition*, V. T. Devita Jr. et al., Eds., Lippincott-Raven, Philadelphia, 333-347 (1997).
Dickson et al., "Growth factors in breast cancer." 1995 *Endocrine Rev.* 16:559-589.
Dohn et al., "Receptor tyrosine kinase EphA2 is regulated by p53-family proteins and induces apoptosis." 2001 *Oncogene.* 20(45):6503-15.
Drescher, "The Eph family in the patterning of neural development," 1997 *Current Biology* 7(12):R799-R807.
Easty et al., "Novel and Known Protein Tyrosine Kinases and Their Abnormal Expression in Human Melanoma." 1993 *J. of Investigative Dermatology* 101:679-684.
Easty et al., "Abnormal protein tyrosine kinase gene expression during melanoma progression and metastasis." 1995 *Intl. J Cancer* 60:129-136.
Easty et al., "Protein B61 as a New Growth Factor: Expression of B61 and Up-Regulation of Its Receptor Epithelial Cell Kinase during Melanoma Progression." 1995 *Cancer Research* 55:2528-2532.
Easty et al., "Loss of Expression of Receptor Tyrosine Kinase Family Genes PTKT and SEK in Metastatic Melanoma." 1997 *Int. J. Cancer* 71:1061-1065.
Easty et al., "Up-regulation of ephrin-A1 during melanoma progression." 1999 *Int J Cancer.* 84(5):494-501.
Easty et al., "Protein tyrosine kinases in malignant melanoma." 2000 *Melanoma Research* 10:401-411.
Eph Nomenclature Committee, "Unified Nomenclature for Eph Family Receptors and Their Ligands, the Ephrins." 1997 *Cell* 90:403-404.
"EPH Receptor Ligands, and Uses Related Thereto" datasheet [online]. The Massachusetts Technology Transfer Center, Boston, MA, copyright date unknown [retrieved on Feb. 28, 2009]. Retrieved from the Internet: <URL:http://www.masstechportal.org/IP4013.aspx>; 1 pg.
"Eph Receptors & Ligands—R&D Systems" datasheet [online]. R&D Systems, Inc., Minneapolis, MN, copyright 2008 [retrieved on Feb. 28, 2009]. Retrieved from the Internet: <URL:http://www.rndsystems.com/mini_review_detail_objectname_MR99_Eph.aspx>; 4 pgs. First printed in R&D Systems' 1999 Catalog.
Ewert et al., "Stability improvement of antibodies for extracellular and intracellular application: CDR grafting to stable frameworks and structure-based framework engineering," in *Methods: a companion to methods in enzymology*. Academic Press; New York, NY: 2004. vol. 34, No. 2, pp. 184-199.
Fan and Mendelsohn, "Therapeutic application of anti-growth factor receptor antibodies," 1998 *Current Opinion in Oncology* 10:67-73.
Fedora-Chaiken et al., "E-cadherin binding modulates EGF receptor activation," Mar. 2003 Cell Commun. Adhes. 10(2):105-108.
Fenrick, "TEL, a Putative Tumor Suppressor, Modulates Cell Growth and Cell Morphology of Ras-Transformed Cells While Repressing the Transcription of *stromelysin-1*." 2000 *Molecular and Cellular Biology* 20(6):5828-5839.
Ferrone et al., eds. *Handbook of Monoclonal Antibodies*, Noges Publications, Park Ridge, N.J., 1985. Chapter 22 and 303-357.
Fidler, "Molecular Biology of Cancer: Invasion and Metastasis." in *Cancer: Principles and Practice of Oncology*, V. T. Devita et al, eds. (Philadelphia: Lippincott-Raven), p. 135-152 (1997).
Foulkes et al., "Purification and characterization of a protein-tyrosine kinase encoded by the Abelson murine leukemia virus." 1985 *J. Biol. Chem.* 260:8070-8077.
Fox et al., "cDNA cloning and tissue distribution of five human Eph-like receptor protein tyrosine kinases." 1995 *Oncogene* 10(5):897-905.
Freshney, *Culture of Animal Cells. A Manual of Basic Technique* 1983;3-4.
Frisch, "Integrins and anoikis." 1997 *Current Opinion in Cell Biology* 9:701-706.
Fry et al., "Inhibitors of protein tyrosine kinases." 1995 *Current Opinion in Biotechnology* 6:662-667.
Gale et al., "Eph receptors and ligands comprise two major specificity subclasses and are reciprocally compartmentalized during embryogenesis." 1996 *Neuron* 17:9-19.
Gale et al., "Ephrins and their receptros: a repulsive topic?" 1997 *Cell Tissue Res.* 290:227-241.
Ganju et al., "The Eck receptor tyrosine kinase is implicated in pattern formation during gastrulation, hindbrain segmentation and limb development." 1994 *Oncogene.* 9(6):1613-1624.
Geiger et al., "Cadherins." 1992 *Annu. Rev. Cell Biol.* 8:307-332.
Genzyme-Techne Corporation, Recombinant Mouse Ephrin-A1/Fc, Catalog No. 3602, Mar. 11, 2003.
George et al., "The VAB-1 Eph receptor tyrosine kinase functions in neural and epithelial morphogenesis in *C. elegans*." 1998 *Cell* 92:633-643.
Gilardi-Hebenstreit et al., "An Eph-related receptor protein tyrosine kinase gene segmentally expressed in the developing mouse hindbrain," Dec. 1992 *Oncogene* 7(12):2499-2506.
Giunciuglio et al., "Invasive phenotype of MCF10A cells overexpressing c-Ha-ras and c-erb-2 oncogenes." 1995 *Intl. J. Cancer* 63:815-822.
Glenney, Jr. et al., "Novel Tyrosine Kinase Substrates from Rous Sarcoma Virus-transformed Cells are Present in the Membrane Skeleton." 1989 *The Journal of Cell Biology* 108:2401-2408.
Goding, *Monoclonal Antibodies: Principles and Practice, Academic Press*, 1986, cover page and pp. 59-103.
Grant, *Synthetic Peptides: A User Guide*, W.H. Freeman and Co., N.Y., 1992, Cover pg., Publication pg., and Table of Contents only.
Gschwind et al., "The discovery of receptor tyrosine kinases: targets for cancer therapy," 2004 *Nature Reviews Cancer* 4:361-370.
Gura, "Systems for Identifying New Drugs are Often Faulty." 1997 *Science* 278:1041-1042.
Gussow et al., "Humanization of monoclonal antibodies." 1991 *Methods Enzymol.* 203:99-121.

(56) References Cited

OTHER PUBLICATIONS

Hamburger, "The Human Tumor Clonogenic Assay as a Model System in Cell Biology." 1987 *International Journal of Cell Cloning* 5:89-107.

Hanahan et al., "The hallmarks of cancer." 2000 *Cell* 100:57-70.

Harlow et al., *Antibodies, A Laboratory Manual*, Cold Spring Harbor Publications, New York, 1988.

Hartwell et al., "Integrating Genetic Approaches into the Discovery of Anticancer Drugs." 1997 *Science* 278:1064-1068.

Hein, "Regulation of Cell Signaling Induced by the Cell Adhesion Molecule, E-Cadherin," Ph.D. Thesis, Purdue University; 94 pgs., Cover Date Aug. 1999. Hardcopy available in Purdue University Library on Nov. 8, 2000.

Helbling et al., "Requirement for EphA receptor signaling in the segregation of Xenopus third and fourth arch neural crest cells." 1998 *Mech Dev.* 78(1-2):63-79.

Henkeneyer et al., "Nuk controls pathfinding of commissural axons in the mammalian central nervous system." 1996 *Cell* 86:35-46.

Henson, "Molecular and genetic targets in early detection." 1999 *Current Opinion in Oncology* 11:419-425.

Hess et al., "Molecular regulation of tumor cell vasculogenic mimicry by tyrosine phosphorylation: Role of epithelial cell kinase (ECK/EphA2)." 2001 *Cancer Res.* 61-3250-3255.

Hill, "Chapter 11: Metastasis" *The Basic Science of Oncology* (Tannock et al., Eds), McGraw-Hill: New York, NY; 1992. pp. 178-195.

Hirai et al., "A novel putative tyrosine kinase receptor encoded by the *eph* gene," Dec. 18, 1987 *Science* 238(4834):1717-1720.

Holder and Klein, "Eph receptors and ephrins: effectors of morphogenesis," 1999 *Development* 126:2033-2044.

Holland et al., "Cell-contact-dependent signalling in axon growth and guidance: Eph receptor tyrosine kinases and receptor protein tyrosine phosphatase beta." 1998 *Curr Opinion Neurobiol.* 8:117-127.

Hoogenboom et al., "By-passing Immunisation Human Antibodies from Syntheti Repertoires of Germline $V_H$ Gene Segments Rearranged in Vitro." 1991 *J. Mol. Biol.* 227:381-388.

Hu et al. "Antibody targeting of the EphA2 receptor tyrosine kinase on breast cancer cells," Meeting Abstract #R6178. 94th Annual Meeting fo the American Association for Cancer Research; Washington D.C., Jul. 11-14, 2003. Proc. of the Am. Assoc. for Cancer Research Jul. 2003; 44(2nd ed):1234.

Hu et al., "EphA2 Induction of Fibronectin Creates a Permissive Microenvironment for Malignant Cells," Oct. 2004 *Molecular Cancer Research* 2(10):533-540.

Huai et al., "Investigation of a Possible Receptor Function of Ephrina Ligands." 2000 *European Journal of Neuroscience*, 12:179.

Hudziak et al., "p185$^{HER2}$ monoclonal antibody has antiproliferative effects in vitro and sensitizes humnan breast cancer tumor cells to tumor necrosis factor," 1989. *Mol. Cell. Biol.*, 9:1165-1172.

Hunter et al., "Novel receptor protein-tyrosine kinases." 1990 *Adv Second Messenger Phosphoprotein* Res.24:260-5.

Hunter et al., "Receptor protein tyrosine kinases and phosphatases." 1992 *Cold Spring Harb Symp Quant Biol.* 57:25-41.

Hunter, "Oncoprotein networks." 1997 *Cell* 88:333-346.

Hutchcroft, "B lymphocyte activation is accompanied by phosphorylation of a 72-kDa protein-tyrosine kinase." 1991 *J. Biol. Chem.* 266:2595-14849.

"ImmunoPure® Monoclonal Antibody Isotyping Kit (HRP/ABTS)" Product Data Sheet. Pierce Biotechnology: Rockford, Illinois. Available online [retrieved Mar. 7, 2008]. Retrieved from the Internet: <http://www.piercenet.com/files/0302as4.pdf>; 4 pages.

"Instructions to Authors" and Table of Contents, *Hybridoma*, Jun. 1998 17(3).

Ireton and Chen, "EphA2 receptor tyrosine kinase as a promising target for cancer therapeutics," 2005 *Current Cancer Drug Targets* 5:149-157.

Jain, "Bathers to Drug Delivery in Solid Tumors." 1994 *Scientific American* 58-65.

Jakobovits et al., "Analysis of homozygous mutant chemeric mice: Delection of the immunoglobulin heav-chain joining region blocks B-cell development and antibody production/" 1993 *Proc. Natl. Acad. Sci. USA* 90:2551-2555.

Jakobovits et al., "Germ-like transmission and expression of a human-derived yeast artificial chromosome." 1993 *Nature* 362:255-258.

Jones, "Replacing the complementarity-determining regions in a human antibody with those from a mouse." 1986 *Nature* 321:522-525.

Kabat et al., "Sequences of Proteins of Immunological Interest," National Institutes of Health, Bethesda, Md. 1987.

Kahn et al., "Immunohistochemical Localization of Epidermal and Mallory Body Cytokeratin in Undifferentiated Epithelial Tumors." 1984 *American Journal of Clinical Pathology* 84:184-191.

Kanner et al., "Monoclonal antibodies to individual tyrosine-phosphorylated protein substrates of oncogene-encoded tyrosine kinases." 1990 *Proc. Natl. Acad. Sci. USA* 87:3328-3332.

Karam et al., "EphA4 is not required for Purkinje cell compartmentation." 2002 *Brain Res Dev Brain Res.* 135(1-2):29-38.

Keely et al., "Integrins and GTPases in tumour cell growth, motility and invasion." 1998 *Trends Cell Biol.* 8:101-106.

Kerr and Thorpe, ed. LabFax Immunochemistry 1994; 115, 157, 191-197.

Kerr et al., *Immunochemistry Labfax*, BIOS Scientific Publishers Ltd., Oxford, England, 1994, title page, copyright page, pp. ix-xi, 185-197.

Khosravi-Far et al., "Activation of Racl, RhoA, and Mitogen-Activated Protein Kinases is Required for Ras Transformation." 1995 *Molecular and Cellular Biology* 15(11)6443-6453.

Kikawa et al., "Regulation of the EphA2 kinase by the low molecular weight tyrosine phosphatase induces transformation." 2002 *J Biol Chem.* 277(42):39274-9.

Kilpatrick et al., "Rapid Development of Affinity Matured Monoclonal Antibodies Using RIMMS." 1997 *Hybridoma*, 16:381-389.

Kilpatrick et al., "Gene Gun Delivered DNA-Based Immunizations Mediate Rapid Production of Murine Monoclonal Antibodies to the Flt-3 Receptor." 1998 *Hybridoma*, 17:569-576.

Kilpatrick et al., "High Affinity Monoclonal Antibodies to PED/PEA-15 Generated Using 5 µg of DNA." 2000 *Hybridoma* 19:297-302.

Kinch et al., "Cell adhesion mediated by CD4 and MHC class II proteins requires active cellular processes." 1993 *J. Immunol.* 151:4552-4561.

Kinch et al., "The protein tyrosine kinase p56$^{lck}$ regulates cell adhesion mediated by CD4 and MHC class II proteins." 1994 *J. Exp Med.* 180:1729-1739.

Kinch et al., "Altered adhesions in ras-transformed breast epitheilal cells." 1995 *Biochem. Soc. Trans.* 23:446-450.

Kinch et al., "Tyrosine phosphorylation regulates the adhesions of ras-transformed breast epithelia," 1995 *J. Cell Biol.* 130:461-471.

Kinch et al., "E-cadherin engagement stimulates tyrosine phosphorylation." 1997 *Cell Adhes. Commun.* 4:425-437.

Kinch et al., "Identification of tyrosine phosphorylated adhesion proteins in human cancer cells," 1998. *Hybridoma.* 17:227-235.

Kinch et al., "Cytometric analysis of cell contact and adhesion." *Cytometry*, Darzynkiewicz et al., Eds., 3$^{rd}$ Ed. Academic Press, San Diego, CA; 2000.

Kinch et al., "Overexpression and functional alterations of the EphA2 tyrosine kinase in cancer." 2003 *Clinical & Experimental Metastasis* 20:59-68.

Kinch et al., "Predictive Value of the EphA2 Receptor Tyrosine Kinase in Lung Cancer Recurrence and Survival." 2003 *Clin Cancer Res.* 9(2):613-8.

Kinch, Michael S., "Characterization of an Adhesion-Associated Tumor Suppressor in Breast Cancer." Grant Abstract, Grant No. BC971054 [online]. 1997 Breast Cancer Research Program Idea Award: United States of America Department of Defense Congressionally Directed Medical Research Programs. Available online [retrieved Apr. 21, 2007]. Retrieved from the Internet: <http://cdmrp.army.mil/scripts/get_item.asp?item=abstract&type=technical&log_no=BC971054>; 1 pg.

(56) References Cited

OTHER PUBLICATIONS

Kinch, Michael S., "Differential Substrate Profile of the EPHA2 Tyrosine Kinase in Non-Transformed and Malignant Breast Epithelia." Grant Abstract, Grant No. BC995027 [online]. 1999 Breast Cancer Research Program Concept Award: United States of America Department of Defense Congressionally Directed Medical Research Programs. Available online [retrieved Apr. 21, 2007]. Retrieved from the Internet: <http://cdmrp.army.mil/scripts/get_item.asp?item=abstract&type=technical&log_no=BC995027>; 1 pg.

Kinch, Michael S., "Antibody Targeting of the EphA2 Kinase on Breast Cancer Cells." Grant Abstract, Grant No. BC000056. 2000 Breast Cancer Research Program Career Development Award: United States of America Department of Defense Congressionally Directed Medical Research Programs. Available online [retrieved Jul. 23, 2007]. Retrieved from the Internet: <http://cdmrp.army.mil/scripts/get_item.asp?item=abstract&type=technical&log_no=BC000056>; 1 pg.

Kinch, Michael S., "Antibody Targeting of the EphA2 Kinase on Breast Cancer Cells." Grant Abstract, Grant No. BC000660. 2000 Breast Cancer Research Program Idea Award: United States of America Department of Defense Congressionally Directed Medical Research Programs. Available online [retrieved Jul. 23, 2007]. Retrieved from the Internet: <http://cdmrp.army.mil/scripts/get_item.asp?item=abstract&type=technical&log_no=BC000660> 1 pg.

Kinch, Michael S., "Regulation of the EphA2 Tyrosine Phosphorylation by the Human Cytoplasmic Protein Tyrosine Phosphatase." Grant Abstract, Grant No. BC995026. 2000 Breast Cancer Research Program Idea Award: United States of America Department of Defense Congressionally Directed Medical Research Programs. Available online [retrieved Jul. 23, 2007]. Retrieved from the Internet: <http://cdmrp.army.mil/scripts/get_item.asp?item=abstract&type=technical&log_no=BC995026>; 1 pg.

Kirk et al., "The human anti-porcine cell mediated response: In vitro studies of function and molecular interaction." 1993 *Transplant* 55(4):924-931.

Kohler et al., "Continous culture of fused cels secreting antibody of predefined specificity." 1975 *Nature* 256:495-497.

Kondapaka et al., "Tyrosine kinase inhibitor as a novel signal transduction and antiproliferative agent: prostate cancer." 1996 *Molecular and Cellular Endocrinology*, 117:53-58.

Koolpe et al., "An ephrin mimetic peptide that selectively targets the EphA2 receptor." 2002 *J Biol Chem.* 277(49):46974-9.

Kozbor et al., "A Human Hybrid Myeloma for Production of Human Monoclonal Antibodies." 1984 *J. Immunol.* 133:3001-3005.

Kratchmarova et al., "Characterization of promoter region and genomic structure of the murine and human genes encoding Src like adapter protein." 2001 *Gene* 262(1-2):267-73.

Lai et al., "An extended family of protein-tyrosine kinase genes differentially expressed in the vertebrate nervous system," May 1991 *Neuron* 6(5):691-704.

Lai et al., "Expression of Eph receptors in skeletal muscle and their localization at the neuromuscular junction." 2001 *Mol Cell Neurosci.* 17(6):1034-47.

Landen et al., "Efficacy and Antivascular Effects of EphA2 Reduction With an Agonistic Antibody in Ovarian Cancer," Nov. 1, 2006 *Journal of the National Cancer Institute* 98(21):1558-1570.

Larrick et al., *Human Hybridomas and Monoclonal Antibodies*; Engleman and Foung, Eds. 1985,Title page, publisher's page, table of contents, and pp. 8-9.

Lawrence, "Mechanisms of tumor invasion and metastasis." 1996 *World J. Urol.* 14:124-130.

Lazar et al., "Transforming Growth Factor : Mutation of Aspartic Acid 47 and Leucine 48 Results in Different Biological Activities." 1988 *Molecular and Cellular Biology* 8(3):1247-1252.

Letwin et al., "Novel protein-tyrosine kinase cDNAs related to *fps/fes* and *eph* cloned using anti-phosphotyrosine antibody," Dec. 1988 *Oncogene* 3(6):621-627.

Levitzki, "Tyrosine Kinase Inhibition: An Approach to Drug Development." 1995 *Science* 267:1782-1788.

Lewis et al., "Differential responses of human tumor cell lines to anti-p185$^{HER2}$ monoclonal antibodies." 1993 *Cancer Immunol. Immunother.* 37:255-263.

Lhotak et al., "Characterization of Elk, a Brain-Specific Receptor Tyrosine Kinase," *Mol. Cell Biol.*, May 1991, 11(5):2496-2502.

Lhotak et al., "Biological and biochemical activities of a chimeric epidermal growth factor-elk receptor tyrosine kinase," Nov. 1993 *Mol. Cell Biol.* 13(11):7071-7079.

Lickliter et al., "Embryonic stem cells express multiple Eph-subfamily receptor tyrosine kinases." 1996 *Proc Natl Acad Sci U S A.* 93(1):145-50.

Lindberg et al., "cDNA Cloning and Characterization of Eck, an Epithelial Cell Receptor Protein-tyrosine Kinase in the Eph/elk Family of Protein Kinases." 1990 *Mol. Cell Biol.* 10(12):6316-6324.

Lu et al., "EphA2 Overexpression Decreases Estrogen Dependence and Tamoxifen Sensitivity," 2003 *Cancer Research* 63:3425-3429.

Magal et al., "B61, a ligand for the Eck receptor protein-tyrosine kinase, exhibits neurotrophic activity in cultures of rat spinal cord neurons," 1996. *J. Neurosci. Res.* 43:735-744.

Maisonpierre et al., "Ehk-1 and Ehk-2: two novel members of the Eph receptor-like tyrosine kinase family with distinctive structures and neuronal expression," Dec. 1993 Oncogene 8(12):3277-3288.

Malik et al., "Integrin-mediated signaling in normal and malignant cells: a role of protein tyrosine kinases." 1996 *Biochimica et Biophysica Acta*, 1287:73-76.

Marks et al., "By-passing immunization. Human antibodies from V-gene libraries displayed on phage." 1991 *J Mol Biol.* 222(3):581-97.

Martone et al., "Immunolocalization of the receptor tyrosine kinase EphA4 in the adult rat central nervous system." 1997 *Brain Res.* 771(2):238-250.

Maru et al., "Overexpression confers an oncogenic potential upon the *eph* gene." 1990 *Oncogene*, 5:445-447.

McBride et al., "Ephrin-A1 is expressed at sites of vascular development in the mouse." 1998 *Mech. Dev.* 77(2):201-204.

McLaughlin, "Functional consequences of coincident expression of EphA receptors and ephrin-A ligands." 1999 *Neuron*. 22(4):636-9.

Miao et al., "Activation of EphA2 kinase suppresses integrin function and causes focal-adhesion-kinase dephosphorylation," *Nature Cell Biol.*, Feb. 2000, 2(2):62-69 and Supplementary Information (2 pages).

Miao et al, "Activation of EphA receptor tyrosine kinase inhibits the Ras/MAPK pathway." 2001 Nat. Cell. Bio. 3:527-530.

Michael et al., "Efficient gene-specific expression of cre recombinase in the mouse embryo by targeted insertion of a novel IRES-Cre cassette into endogenous loci." 1999 *Mech Dev*. 85(1-2):35-47.

Miller et al., "Xenograft model of progressive human proliferative breast disease." 1993 *J. Natl Cancer Instit.* 85:1725-1732.

Miller et al., "The engagement of $\beta_1$ integrins on promonocytic cells promotes phosphorylation of Syk and formation of a protein complex containing Lyn and $\beta_1$ integrin." 1999 *Eur. J. Immuno*. 29:1426-1434.

Miller et al., "EA5, novel EphA2-targeted monoclonal antibody, inhibits growth and metastasis in human breast cancer xenografts," Meeting Abstract #561. 96$^{th}$ *Annual Meeting of the American Association for Cancer Research*; Anaheim, CA: Apr. 16-20, 2005 *Proc. of the Am. Assoc. for Cancer Research* Jul. 2005; 46:132. Available online [retrieved Mar. 10, 2008]. Retrieved from the Internet: <http://www.aacrmeetingabstracts.org/cgi/content/abstract/2005/1/132-a?maxtoshow=&HITS=10&hits=10&RESULTFORMAT=1&author1=Miller&title=EphA2&andorexacttitle=and&andorexacttitleabs=and&searchid=1&FIRSTINDEX=0&sortspec=relevance&resourcetype=HWCIT>; 2 pgs.

Miyazaki et al., "EphA2 overexpression correlates with poor prognosis in esophageal squamous cell carcinoma." 2003 *Int J Cancer.* 103(5):657-63.

Morrison et al., "Chimeric human antibody molecules: Mouse antigen-binding domains with human constant region domains." 1984 *Proc. Natl. Acad. Sci. USA*, 81:6851-6855.

Muhlbauer et al., "Detection of melanoma cells in the blood of melanoma patients by melanoma-inhibitory activity (MIA) reverse transcription-PCR." 1999 *Clinical Cancer Research* 5(5):1099-1105.

(56) References Cited

OTHER PUBLICATIONS

Munson et al., "LIGAND: A Versatile Computerized Approach for Characterization of Ligand-Binding Systems." 1980 *Anal. Biochem.* 107:220-239.
Murphy et al., "Epidermal growth factor gene expression in human breast cancer cells: regulation of expression by progestins." 1988 *Cancer Res.* 48:4555-4560.
Nakamoto, "Eph receptors and ephrins."2000 *IJBCB* 32:7-12.
Nakamoto et al., "Diverse roles for the Eph family of receptor tyrosine kinases in carcinogenesis." 2002 *Microsc Res Tech.* 59(1):58-67.
Naruse-Nakajima et al., "Involvement of EphA2 in the formation of the tail notochord via interaction with ephrinA1." 2001 *Mech Dev.* 102(1-2):95-105.
NCBI Locus Link search for "B61" performed Nov. 24, 2003. Http://www.mcbi.nlm.nih.gov/LocusLink/list.cgi paper copy present.
Nemoto et al., "Overexpression of Protein Tyrosine Kinases in Human Esphageal Cancer." 1997 *Pathobiology* 65:195-203.
New England Biolabs Product Catalog No. 800, 1996, p. 164. Protein Fusion and Purification System.
Nishida et al., "Domain-specific olivocerebellar projection regulated by the EphA-ephrin-A interaction." 2002 *Development* 129(24):5647-58.
Nose et al., "Expressed recombinant cadherins mediated cell sorting in model systems." 1988 *Cell* 54:993-1001.
Nowakowski et al., "Structures of the Cancer-Related Aurora-A, FAK, and EphA2 Protein Kinases from Nanovolume Crystallography." 2002 *Structure* 10(12):1659-67.
O'Brien et al., "A mechanism for trabecular meshwork cell retraction: Ethacrynic acid initiates the dephosphorylation of focal adhesion proteins." 1997 *Exp. Eye Res.* 65:471-483.
Oettgen et al., "The History of Cancer Immunotherapy." *Biologic Therapy of Cancer*, Devita et al. eds., Lippincott, Philadelphia, Chapter 6, pp. 87-119; 1991.
Ogawa et al., "The ephrin-A1 ligand and its receptor. EphA2, are expressed during tumor neovascularization." 2000 *Oncogene* 19(52):6043-52.
Ohta et al., "The receptor tyrosine kinase, Cek8, is transiently expressed on subtypes of motoneurons in the spinal cord during development." 1996 *Mechanisms Devel.* 54(1):59-69.
On-line Medical Dictionary "Agonist," Published at the Dept. of Medical Oncology, University of Newcastle upon Tyne Published on Nov. 18, 1997, [retrieved on Jul. 31, 2002] Retrieved from the Internet: <http://medical-dictionary.com/dictionaryresults.php>; 1 pg.
Orlandi et al., "Cloning Immunoglobulin Variable Domains for Expression by the Polymerase Chain Reaction," May 1989 PNAS 86:3833-3837.
Orsulic et al., "Expression of Eph receptors and ephrins is differentially regulated by E-cadherin." 2000 *J Cell Sci.* 113:1793-802.
Oslo et al., *Remington's Pharmaceutical Science*, 16$^{th}$ ed., Mack Publishing Co.: Easton, PA, 1980: Table of Contents and Cover Page.
Owens et al., "Overexpression of focal adhesion kinase (p125$^{FAK}$) in invasive human tumors." 1995 *Cancer Res.* 55:2752-2755.
Ozawa et al., "A possible new adhesive site in the cell-adhesion molecule uvomorulin." 1991 *Mech. Dev.* 33:49-56.
Paine et al., "Characterization of ephithelial phenotypes in mortal and immortal human breast cells." 1992 *Int. J. Cancer* 50:463-473.
Pandey et al., "Activation of the Eck receptor protein tyrosine kinase stimulates phosphatidylinositol 3-kinase activity." 1994 *J. Biol. Chem.* 269:30154-30157.
Pandey et al., "Characterization of a novel src-like adapter protein that associates with the Eck receptor tyrosine kinase." 1995 *J. Biol. Chem.* 270:19201-19204.
Pandey et al., "Role of B61, the ligand for the Eck receptor tyrosine kinase, in TNF-α-induced angiogeneis." 1995 *Science* 269:567-569.
Parsons et al., "Protein-tyrosine kinases, oncogenes, and cancer." 1993 *Important Adv. Oncol.* 3-17.
Parsons, "Integrin-mediated signaling: regulation by protein tyrosine kinases and small GTP-binding proteins." 1996 *Curr. Opin. Cell Biol.* 8:146-152.
Pasquale, "Identification of chicken embryo kinase 5, a developmentally regulated receptor-type tyrosine kinase of the Eph family," Jul. 1991 *Cell Regulation* 2(7):523-534.
Pasquale, "The Eph family of receptors." 1997 *Current Opinion in Cell Biology* 9:608-615.
Patarca (Ed.), "Protein Phosphorylation and Dephosphorylation in Physiologic and Oncologic Processes." 1996 *Critical Reviews in Oncogenesis*, 7:343-432.
Pauley et al., "The MCF10 family of spontaneously immortalized human breast epithelial cell lines: models of neoplastic progression." 1993 *Eur J. Cancer Prev 2 Suppl*, 3:67-76.
Pegram et al., "Antibody dependent cell-mediated cytotoxicity in breast cancer patients in Phase III clinical trials of a humanized anti-HER2 antibody." Abstract #4044. 88$^{th}$ Annual Meeting of the American Association of Cancer Research. Apr. 12-16, 1997; San Diego, CA. Published in: 1997 *Proc. Am. Assoc. Cancer Res.* 38:602.
Pegram et al., "HER-2/neu as a predictive marker of response to breast cancer therapy." 1998 *Breast Cancer Res. Treat.* 52:65-77.
Potla et al., "Reduced expression of EphrinA1 (EFNA1) inhibits three-dimensional growth of HT29 colon carcinoma cells." 2002 *Cancer Lett.* 175(2):187-95.
Pratt et al., "Activation of the EphA2 tyrosine kinase stimulates the MAP/EEK kinase signaling cascade." 2002 *Oncogene* 21(50):7690-9.
Press et al., "HER-2/neu Oncogene Amplification and Expression in Breast and Ovarian Cancers." 1990 *Prog. Clin. & Biol. Res.* 354A:209-221.
Presta, "Antibody engineering." 1992 *Current Op. Struct. Biol.* 2:593-596.
Presta et al., "Humanization of an Antibody Directed Against IgE." 1993 *J. Immunol.* 151:2623.
Price, "Analysing the metastatic phenotype." 1994 *J. Cell Biochem.* 56:16-22.
Price, "Metastasis from human breast cancer cell lines." 1996 *Breast Cancer Res. Treat.* 39:93-102.
R&D Systems, "Recombinant Mouse Ephrin-A1/Fc Chimera" Catalog No. 602-A1. Apr. 30, 2002.
Rajarathnam et al., "H NMR Studies of Interleukin 8 Analogs: Characterization of the Domains Essential for Functions." 1994 *Biochemistry* 33:6623-30.
Rhim et al., "Human Prostate Carcinogenesis." 1997 *Crit. Rev. Oncog.* 8:305-328.
Riechmann et al., "Reshaping human antibodies for therapy." 1988 *Nature* 332:323-327.
Roche et al., "Sre-like adaptor protein (SLAP) is a negative regulator of mitogenesis." 1998 *Current Biol.* 8:975-978.
Rosenberg et al., "Epithelial cell kinase-B61: an autocrine loop modulating intestinal epithelial migration and barrier function." 1997 *Am. J. Physiol.* 273:G824-G832.
Rosenberg, "Principles of Cancer Management: Surgical Oncology." *Cancer: Principles and Practice of Oncology, Fifth Edition*, V. T. Devita, Jr. et al., Eds., Lippincott-Raven, Philadelphia, 1997:cover page, table of contents and 295-306.
Rudikoff et al., "Single amino acid substitution altering antigen-binding specificity." 1982 *Proc Natl Acad Sci U S A* 79(6):1979-83.
Ruiz et al., "The expression of the receptor-protein tyrosine kinase gene, eck, is highly restricted during early mouse development." 1994 *Mech Dev.* 46(2):87-100.
Ruoslahti, "Cell adhesion and tumor metastasis." 1994 *Princess Takamatsu Symp*, 24:99-105.
Ruoslahti, "Fibronectin and Its Integrin Receptors in Cancer." 1999 *Advances in Cancer Research* 76:1-20.
Sajjadi et al., "Identification of a new *eph*-related receptor tyrosine kinase gene from mouse and chicken that is developmentally regulated and encodes at least two isoforms of the receptor," Aug. 1991 *New Biol.* 3(8):769-778.
Sajjadi et al., "Five novel avian Eph-related tyrosine kinases are differentially expressed," Jul. 1993 *Oncogene* 8(7):1807-1813.
Sarosdy et al., "Prediction of Response to Cancer Chemotherapy." 1983 *Drugs* 26:454-459.

(56) References Cited

OTHER PUBLICATIONS

Schick et al., "Anti-TAPA-1 antibodies induce protein tyrosine phosphorylation that is prevented by increasing intracellular thiol levels," 1993. *J. Immunol.* 151(4):1918-1925.
Schlaepfer et al., "Signal transduction from the extracellular matrix-a role for the focal adhesion protein-tyrosine kinase FAK." 1996 *Cell Structure Function* 21:445-450.
Schlessinger, "Signal transduction by allosteric receptor oligomerization," Nov. 1988 Trends Biol. Sci. 13:443-447.
Schnölzer et al., "Constructing Proteins by Dovetailing Unprotected Synthetic Peptides: Backbone-Engineered HIV Protease." 1992 *Science* 256:221-225.
Scully et al., "Isolation and characterization of Desk, a *Drosophila* eph receptor protein tyrosine kinase." 1999 *Mol Cell. Neuro.* 13(5):337-347.
Shak, "Overview of the trastuzumab (Herceptin) anti-HER2 monoclonal antibody clinical program in HER2-overexpressing metastatic breast cancer." 1999 *Seminars Oncol.* 26:71-77.
Sims et al., "A Humanized CD18 Antibody Can Bock Funciton without Cell Destruction." 1993 *J. Immunol.* 151:2296.
Slamon et al., "Studies of the HER-2/neu Proto-oncogene in Human Breast and Ovarian Cancer." 1989 *Science* 244:707-712.
Sliwkowski et al., "Nonclinical Studies Addressing the Mechanism of Action of Trastuzumab (Herceptin)." 1999 *Seminars in Oncology* 26:60-70.
Smith et al., "Cardiac Glycoside-Specific Antibodies in the Treatment of Digitalis Intoxication." 1977 *Antibodies in Human Diagnosis and Therapy* 365-389.
Smith et al., "Phage Display," *Chem Rev.* 1997, 97:391-410.
Southern et al., "Transformation of mammalian cells to antibiotic resistance with a bacterial gene under control of the SV40 early region promoter." 1982 *J. Mol. Appl. Genet.* 1:327-341.
Stearns et al., "Human xenograft models for prostate cancer." 1998 *The Prostate* 36:56-58.
Steeg et al., "Molecular analysis of premalignant and carcinoma in situ lesions of the human breast." 1996 *Am J Pathology* 149:733-738.
Stein et al., "Eph receptors discriminate specific ligand oligomers to determine alternative signaling complexes, attachment, and assembly responses." 1998 *Genes Dev.* 12(5):667-78.
Stein et al., "Nck recruitment to Eh receptor, EphB1/ELK couples ligand activation to c-JUN kinase." 1998 *J. Biol. Chem.* 273:1303-1308.
Straume et al., "Importance of vascular phenotype by basic fibroblast growth factor, and influence of the angiogenic factors basic fibroblast growth factor/fibroblast growth factor receptor-1 and ephrin-A1/EphA2 on melanoma progression." 2002 *Am J Pathol.* 160(3):1009-19.
Studer et al., "Genetic interactions between Hoxa1 and Hoxb1 reveal new roles in regulation of early hindbrain patterning." 1998 *Development.* 125(6):1025-36.
Sulman et al., "ECK, a human EPH-related gene, maps to 1p36.1, a common region of alteration in human cancers." 1997 *Genomics* 40(2):371-4.
Surawska et al., "The role of ephrins and Eph receptors in cancer," 2004 *Cytokine & Growth Factor Reviews* 15:419-433.
Terstappen et al., "Flow Cytometry—Principles and Feasability in Transfusion Medicine. Enumeration of Epithelial Derived Tumor Cells in Peripheral Blood." 1998 *Vox Sanguinis* 74(suppl. 2): 269-274.
van der Geer et al., "Receptor Protein-Tyrosine Kinases and Their Signal Transduction Pathways." 1994 *Annu. Rev. Cell Biol.* 10:251-337.
Varmus et al., "Biochemical mechanisms of oncogene activity: proteins encoded by oncogenes." 1986 *Cancer Surv.* 5:153-158.
Verhoeyen et al., "Reshaping Human Antibodies: Grafting an Antilysozyme Activity." 1988 *Science* 239:1534-1536.
Vestweber et al., "Rabbit antiserum against a purified surface glycoprotein decompacts mouse preimplanted embryos and reacts with specific adult tissues." 1984 *Exp. Cell Res.* 152:169-178.
Vestweber et al., "Some structural and functional aspects of the cell adhesion molecule uvomorulin."1984 *Cell Differ.* 15:269-273.
Vestweber et al., "Identification of a putative cell adhesion domain of uvomorulin." 1985 *EMBO J.* 4:3393-3398.
Vignali et al., "Interactions of CD4 with MHC class II molecules, T cell receptors and p56lck." 1993 *Phil. Trans. Royal Soc. London* 342:13-24.
Vitetta and Uhr, "Monoclonal antibodies as agonists: an expanded role for their use in cancer therapy," Oct. 15, 1994 *Cancer Research* 54:5301-5309.
Volberg et al., "The effect of tyrosine-specific protein phosphorylation on the assembly of adherens-type junctions." 1992 *EMBO J.* 11:1733-1742.
Wada et al., "Glycosylphosphatidylinositol-anchored cell surface proteins regulate position-specific cell affinity in the limb bud." 1998 *Devel. Biol.* 202(2):244-252.
Walker-Daniels et al., "Overexpression of the EphA2 Tyrosine Kinase in Prostate Cancer." 1999 *Prostate* 41(4):275-280.
Walker-Daniels, "Overexpression of EphA2 in Metastatic Cancer Cells: A Role for Ras Signaling," Mol, Bio. Cell, 10, abstract 2469 (1999); 39.sup.th American Society for Cell Biology, (Dec. 11-15, 1999).
Walker-Daniels et al., "The Mechanism of EphA2 Protein Degradation: Implications of Increased EphA2 Protein Levels in Metastatic Cancer Cells,"Abstract #4511 Proceedings of the American Association for Cancer Research Annual Meeting, 2001.
Walker-Daniels, "The Regulation of Elevated EphA2 Protein Levels in Metastatic Cancer Cells: Roles for Ligand Binding, Protein Degradation, and c-Cbl," PhD. thesis, Purdue University, 119 pages. Cover Date Dec. 2001.
Walker-Daniels et al., "c-Cbl-Dependent EphA2 Protein Degradation Is Induced by Ligand Binding." 2002 *Mol Cancer Res.* 1(1):79-87.
Walker-Daniels et al., "Differential Regulation of EphA2 in Normal and Malignant Cells." 2003 Am. J. Pathology 162(4):1037-1042.
Wang et al., "Negative regulation of EphA2 receptor by Cbl." 2002 *Biochem Biophys Res Commun.* 296(1):214-20.
Waters et al., "Spontaneous Metastasis of PC-3 Cells in Athymic Mice After Implantation in Orthotopic or Ectopic Microenvironments." 1995 *Prostate* 26:227-234.
Weaver et al., "The development of a functionally relevant cell culture model of progressive human breast cancer." 1995 *Semin. Cancer Biol.* 6:175-184.
Weiner, "Monoclonal antibody therapy of cancer." 1999 *Seminars Oncol.* 26:43-51.
Wendling et al., "Retinoid signaling is essential for patterning the endoderm of the third and fourth pharyngeal arches." 2000 *Development.* 127(8):1553-62.
Wicks et al., "Molecular cloning of HEK, the gene encoding a receptor tyrosine kinase expressed by human lymphoid tumor cell lines," Mar. 1, 1992 *PNAS* 89(5):1611-1615.
Zantek et al., "Identification of an adhesion-associated tyrosine kinase that is tightly regulated in breast cancer," 37th Annual Meeting of the American Society for Cell Biology. Abstract 777. Washington D.C.: Dec. 13-17, 1997.
Zantek et al., "Epithelial cell kinase (ECK/EPHA2) regulation in breast cancer," 38th Annual Meeting of the American Society for Cell Biology. Abstract 773. San Francisco, CA: Dec. 12-16, 1998.
Zantek et al., "Regulation of the EphA2 receptor tyrosine kinase by estrogen and myc," Proceedings of the American Assoc. for Cancer Research Annual, 40:687, abstract 4537; 90th Annual Meeting of the American Association for Cancer. Apr. 10-14, 1999.
Zantek et al., "E-Cadherin regulates the function of the EphA2 receptor tyrosine kinase," 1999. *Cell Growth & Differentiation.* 10(9):629-638.
Zantek, "Regulation of EphA2 and Focal Adhesion Kinase in Breast Cancer," Ph.D. thesis, Purdue University; 136 pages. cover dated May 1999. Hardcopy available in Purdue University Library on Nov. 8, 2000.
Zantek et al., "Chapter 25: Analysis of Cell Migration," *Methods in Cell Biology*, vol. 63, *Cytometry, Third Edition, Part A*, Darzynkiewicz et al., eds., Academic Press, San Diego, CA, 2001; title page, publication page, table of contents and pp. 549-559.

(56) References Cited

OTHER PUBLICATIONS

Zantek et al., "MCF-10A-NeoST: A New Cell System for Studying Cell-ECM and Cell-Cell Interactions in Breast Cancer." 2001 *Clinical Cancer Research* 7:3640-3648.

Zelinski et al., "EphA2 Overexpression Causes Tumorigenesis of Mammary Epithelial Cells." 2001 *Cancer Research* 61:2301-2306.

Zelinski, "Overexpression of the Receptor Tyrosine Kinase EphA2 Induces Malignant Transformation of Benign Mammary Epithelial: Implication for Increased Cell Survival and Altered Cellular Adhesions in Breast Cancer," PhD. thesis, Purdue University, 131 pages. Cover Date Dec. 2001.

Zelinski et al., "Estrogen and Myc Negatively Regulate Expression of the EphA2 Tyrosine Kinase." 2002 *Journal of Cellular Biology* 85:714-720.

Zhang et al., "Relative malignant potential of human breast carcinoma cell lines established from pleural effusions and a brain metastasis." 1991 *Invasion Metastasis* 11:204-215.

Zhong et al., "Rho-stimulated contractility contributes to the fibroblastic phenotype of ras-transformed epithelial cells." 1997 *Mol. Biol. Cell.* 8:2329-2344.

Zhou, "The Eph family receptors and ligands," 1998 Pharmacol. Ther. 77(3):151-181.

Zisch et al., "Complex formation between EphB2 and Src requires phosphorylation of tyrosine 611 in the EphB2 juxtamembrane region" 1998 *Oncogene*, 16:2657-2670.

Zoller et al., "Olgonucleotide-directed mutagenesis using M13-derived vectors: an efficient and general procedure for the production of point mutations in any fragment of DNA" 1982 *Nucl. Acids Res.* 10:6487-6500.

Office Action dated Jul. 5, 2001, for U.S. Appl. No. 09/640,952; 6 pgs.

Office Action dated Jan. 2, 2002, for U.S. Appl. No. 09/640,952; 6 pgs.

Office Action dated Oct. 22, 2002, for U.S. Appl. No. 09/640,952; 6 pgs.

Office Action dated Jun. 19, 2003, for U.S. Appl. No. 09/640,952; 11 pgs.

Office Action dated Apr. 21, 2004, for U.S. Appl. No. 09/640,952; 12 pgs.

Office Action dated Dec. 15, 2004, for U.S. Appl. No. 09/640,952; 8 pgs.

Office Action dated Jun. 17, 2005, for U.S. Appl. No. 09/640,952; 6 pgs.

Office Action dated Dec. 23, 2005, for U.S. Appl. No. 09/640,952; 10 pgs.

Office Action dated Aug. 9, 2006, for U.S. Appl. No. 09/640,952; 5 pgs.

Office Action dated Oct. 7, 2008, for U.S. Appl. No. 11/716,792; 16 pgs.

Office Action dated May 28, 2009, for U.S. Appl. No. 11/716,792; 16 pgs.

Office Action dated Feb. 18, 2010, for U.S. Appl. No. 11/716,792; 16 pgs.

International Search Report mailed Feb. 13, 2001, for International Application No. PCT/US00/22669; 6 pgs.

Written Opinion mailed Sep. 14, 2001, for International Application No. PCT/US00/22669; 4 pgs.

International Preliminary Examination Report completed Nov. 20, 2001, for International Application No. PCT/US00/22669; 5 pgs.

Office Action dated May 6, 2002, for U.S. Appl. No. 09/640,935; 6 pgs.

Office Action dated Aug. 14, 2002, for U.S. Appl. No. 09/640,935; 15 pgs.

Office Action dated May 23, 2003, for U.S. Appl. No. 09/640,935; 6 pgs.

Office Action dated Mar. 9, 2004, for U.S. Appl. No. 09/640,935; 10 pgs.

Office Action dated Sep. 20, 2007, for U.S. Appl. No. 11/063,101; 6 pgs.

Office Action dated Jul. 8, 2008, for U.S. Appl. No. 11/063,101; 6 pgs.

Office Action dated Nov. 18, 2008, for U.S. Appl. No. 11/063,101; 7 pgs.

Office Action dated Jul. 8, 2009, for U.S. Appl. No. 11/063,101; 6 pgs.

Office Action dated Sep. 20, 2007, for U.S. Appl. No. 11/297,548; 7 pgs.

Office Action dated Jul. 10, 2008, for U.S. Appl. No. 11/297,548; 7 pgs.

Office Action dated Mar. 12, 2009, for U.S. Appl. No. 11/297,548; 7 pgs.

Office Action dated Sep. 15, 2009, for U.S. Appl. No. 11/297,548; 7 pgs.

International Search Report mailed Jan. 16, 2001 for International Application No. PCT/US00/22670; 4 pgs.

Written Opinion mailed Nov. 16, 2001 for International Application No. PCT/US00/22670; 7 pgs.

International Preliminary Examination Report completed Jan. 22, 2002 for International Application No. PCT/US00/22670; 8 pgs.

"Annex A" (1 page) from the Reply of the Patent Proprietor to the Notice(s) of Opposition, submitted to the European Patent Office, Opposition Division, in the opposition proceeding regarding EP 1 242 060/EP Pat. Appl. No. 00 955 687.9, Sep. 24, 2007.

Decision of the European Patent Office, Opposition Division, revoking EP 1 242 060/EP Pat. Appl. No. 00 955 687.9: EPO Form 2331 (2 pages) and EPO Form 2918 (12 pages), Dec. 23, 2008.

Freshney, *Culture of Animal Cells: A Manual fo Basic Technique.* 3$^{rd}$ Edition. John Wiley & Sons, Inc.: New York, NY; 1994. Cover page and p. 352.

Kvalheim, "Detection of occult cells in bone marrow and blood in breast cancer patients," 1996 *Acta Oncol.* 35(Supp 8):13-18.

Office Action issued in U.S. Appl. No. 11/716,792, and mailed on Jul. 8, 2010.

Ray et al., "Generation of a fusion partner to sample the repertoire of splenic B cells destined for apoptosis," Jun. 1994 *Proc. Natl. Acad. Sci. USA* 91:5548-5551.

Shao et al., "Characterization of B61, the ligand for the Eck receptor protein-tyrosine kinase," Mar. 10, 1995 *J. Biol. Chem.* 270(10):5636-5641.

Kozlosky et al., "LERK-7: a ligand of the Eph-related kinases is developmentally regulated in the brain," 1997 *Cytokine* 9:540-549.

Asem, Elikplimi K., "Regulation of the EphA2 Tyrosine Phosphorylation by the Human Cytoplasmic Protein Tyrosine Phosphatase." Jun. 2002 Final Report prepared for Grant DAMD17-01-1-0610: awarded by the U.S. Army Medical Research and Materiel Command. Document declassified on Dec. 4, 2002. Available online [retrieved Aug. 5, 2011]. Retrieved from the Internet: <http://www.dtic.mil/dtic/tr/fulltext/u2/b282209.pdf>; 36 pages.

Kinch, Michael S., "Differential Substrate Profile and the EphA2 Tyrosine Kinase in Non-transformed and Malignant Breast Epithelia." Mar. 2002 Final Report prepared for Grant DAMD17-00-1-0652: awarded by the U.S. Army Medical Research and Materiel Command; 7 pages.

Kinch, Michael S., "Characterization of an Adhesion Associate Tumor Suppressor in Breast Cancer." Aug. 1999 Annual Report prepared for Grant DAMD17-98/1/8146: awarded by the U.S. Army Medical Research and Materiel Command. Document declassified on Aug. 26, 2002. Available online [retrieved Jul. 19, 2011]. Retrieved from the Internet: <http://www.dtic.mil/cgi-bin/GetTRDoc?Location=U2&doc=GetTRDoc.pdf&AD=ADB261527>; 57 pages.

Kinch, Michael S., "Characterization of an Adhesion Associate Tumor Suppressor in Breast Cancer." Aug. 2000 Annual Report prepared for Grant DAMD17-98-1-8146: awarded by the U.S. Army Medical Research and Materiel Command; 34 pages.

Kinch, Michael S., "Characterization of an Adhesion Associate Tumor Suppressor in Breast Cancer." Aug. 2001 Final Report prepared for Grant DAMD17-98-1-8146: awarded by the U.S. Army Medical Research and Materiel Command. Document declassified on Aug. 26, 2002. Available online [retrieved Aug. 5, 2011]. Retrieved from the Internet:< http://www.dtic.mil/dtic/tr/fulltext/u2/b274286.pdf5; 52 pages.

(56) References Cited

OTHER PUBLICATIONS

Office Action dated Mar. 17, 2011, for U.S. Appl. No. 11/716,792; 12 pgs.

Weber, Georg, F., "A Molecular Connection between Breast Cancer Proliferation and Metastasis Mediated by Akt Kinase," Aug. 2006 Final Report prepared for Grant DAMD17-2-1-0510: awarded by the U.S. Army Medical Research and Materiel Command. Document declassified on Aug. 26, 2002. Available online [retrieved Jul. 19, 2011]. Retrieved from the Internet: < http://www.dtic.mil/dtic/tr/fulltext/u2/a458463.pdf>; 42 pages.

* cited by examiner

- Inject Lymph Nodes Every Other Day for 10 Days
- Harvest Lymph Node Cells
- Fuse with Myeloma Overexpressing Bcl-2
- Screen by Immunofluorescence Microscopy
- Select for Antigen with Sites of Cell Adhesion:
  - Cell-Cell or
  - Cell-ECM/Membrane Ruffles

EPHA2 AS A THERAPEUTIC TARGET FOR CANCER

This application is a continuation application under 37 CFR §1.53(b) of Ser. No. 11/063,101, filed on Feb. 22, 2005 (now abandoned), which is a continuation of U.S. patent application Ser. No. 09/640,935, filed 17 Aug. 2000 (now issued as U.S. Pat. No. 6,927,203), which claims the benefit of U.S. Provisional Patent Application Ser. No. 60/149,258, filed 17 Aug. 1999.

GOVERNMENT FUNDING

The present invention was made with government support under Grant No. DAMD 17-98-1-8146, awarded by Army Breast Cancer. The Government has certain rights in this invention.

FIELD OF THE INVENTION

The present invention relates to diagnosis and treatment of metastatic disease. More particularly, this invention relates to the use of an epithelial cell tyrosine kinase that is overexpressed in metastatic tumor cells as the target for the diagnosis and treatment of metastatic disease. Most particularly, this invention relates to the use of compounds that interact with and alter expression of the epithelial cell tyrosine kinase.

BACKGROUND AND SUMMARY OF THE INVENTION

Cancer is a disease of aberrant signal transduction. The most dangerous fowls of cancer are malignant cells that metastasize to distant sites in a body. Metastatic cells have acquired the ability to break away from the primary tumor, translocate to distant sites, and colonize distant and foreign microenvironments. Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions. Cell adhesions control the physical interactions of cells with their microenvironment. Cell adhesions also initiate signals that dictate tumor cell growth, death, and differentiation. At the cellular level, metastatic cells have overcome restraints upon cell growth and migration that result from physical linkages and signals conveyed by cell-cell contacts. Malignant cells often have increased interactions with surrounding extracellular matrix (ECM) proteins that provide linkages and signals that promote several aspects of metastasis.

Levels of protein tyrosine phosphorylation regulate a balance between cell-cell and cell-ECM adhesions in epithelial cells. Elevated tyrosine kinase activity weakens cell-cell contacts and promotes ECM adhesions. Alteration in levels of tyrosine phosphorylation is believed to be important for tumor cell invasiveness. Tyrosine phosphorylation is controlled by cell membrane tyrosine kinases, and increased expression of tyrosine kinases is known to occur in metastatic cancer cells.

EphA2 is a 130 kDa receptor tyrosine kinase that is expressed on adult epithelia. A member of the Eph family of tyrosine kinases known as Ephrins, EphA2 is a transmembrane receptor tyrosine kinase with a cell-bound ligand. EphA2 expression has been found to be altered in many metastatic cells, including lung, breast, colon, and prostate tumors. Additionally, the distribution and/or phosphorylation of EphA2 is altered in metastatic cells. Moreover, cells that have been transformed to overexpress EphA2 demonstrate malignant growth, and stimulation of EphA2 is sufficient to reverse malignant growth and invasiveness. EphA2 is a powerful oncoprotein. The present invention is directed to compounds and methods that target EphA2 for the diagnosis and treatment of metastatic cancers.

One approach to cancer therapy is the administration of preformed antibodies to predetermined tumor antigens. This process is known as passive antibody treatment. An example of passive antibody treatment is the use of Herceptin® for the treatment of breast cancer. Herceptin® is a humanized form of a murine monoclonal antibody specific for the extracellular domain of Her2/Neu. The basis for treatment with Herceptin® is that 25-30% of metastatic breast cancers overexpress the Her2/Neu receptor tyrosine kinase. Herceptin® has been well tolerated in clinical trials and shows much promise for the maintenance and regression of metastatic breast cancer.

Effective passive immunotherapy for treatment of tumors requires isolation and preparation of an antibody that: 1) targets an antigen that is overexpressed in metastatic tumors; 2) targets an extracellular epitope of said antigen; 3) is not cross-reactive with any other antigen in a patient's circulation; and 4) exhibits tumoricidal or tumoristatic activity.

In a preferred embodiment, this invention relates to the selection and use of antibodies that are specific to an extracellular epitope of EphA2. The methods of this invention include the preparation, selection, and use of EphA2 specific antibodies for cancer therapy.

Another approach to cancer treatment is to use agonists to stimulate expression. For example, EphrinA1-$F_c$, the extracellular domain of ephrinA1 linked to immunoglobulin heavy chain, (see Miao, H., et al., EphA2 kinase associates with focal adhesion kinase and upon activation, inhibits integrin-mediated cell adhesion and migration, Nature Cell Biol 2, 62-69 (2000), hereby incorporated by reference) can be used to increase the phosphotyrosine content of EphA2. Thus, in another preferred embodiment, this invention relates to the use of agonists or antagonists to alter the expression of EphA2 in metastatic cells.

Thus, this invention is directed to the use of agonists and antagonists to alter the expression of EphA2. EphA2 may be targeted by use of artificial or hybrid forms of the protein, protein inhibitors, antisense oligonucleotides, or small molecule inhibitors. Also, while a preferred embodiment is directed to use of monoclonal antibodies, polyclonal, artificial, and hybrid antibodies are known in the art. It should be understood that use of techniques known in the art to target EphA2 are within the scope of this invention.

One aspect of this invention is a pharmaceutical composition for the treatment of mammalian metastatic tumors which overexpress EphA2, comprising a compound that specifically interacts with an extracellular epitope of EphA2 in an amount effective to reduce metastatic disease and a pharmaceutically acceptable carrier. In the preferred embodiment, the pharmaceutical composition comprises the antibody B2D6, an antibody that specifically binds to an extracellular epitope of EphA2

Another aspect of this invention is a method of treating a patient having a metastatic tumor which overexpresses EphA2. The method comprises administering to the patient a therapeutic amount of a compound that binds to an extracellular epitope of EphA2. In a preferred embodiment, the compound is an antibody.

A third aspect of this invention is a method for detecting the presence of metastatic cells. The method includes use of a labeled antibody specific to an extracellular epitope of EphA2. A cell sample is incubated with the antibody, unbound antibody is removed, and the bound labeled antibody is detected.

An additional aspect of this invention is a method for producing antibodies which inhibit metastatic tumor proliferation by specifically binding to an extracellular epitope of EphA2. This method includes injecting tyrosine phosphorylated proteins into the lymph nodes of a mammal, harvesting the lymph nodes, fusing the lymph node cells with myeloma cells to form hybridomas, and selecting hybridomas which produce antibodies specific for EphA2.

In still another aspect of this invention, a pharmaceutical composition for treatment of a mammalian metastatic tumor is provided, the composition comprising a compound that alters expression of EphA2 in an amount effective to reduce metastatic proliferation of said tumor, and a pharmaceutically acceptable carrier therefor. In a preferred embodiment, the composition comprises an ephrin.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 2A is a western blot showing EphA2 expression in various human prostate cancer cell lines;

FIG. 2B is similar to FIG. 2A, except showing EphA2 expression in a human prostatic epithelial cell line and expression in the cell line after transformation by oncogenic K-Ras or X-irradiation;

FIG. 2C is similar to FIG. 2B, except showing EphA2 expression in another human prostatic epithelial cell line and expression in the cell line after transformation by oncogenic K-Ras or X-irradiation;

DETAILED DESCRIPTION OF THE INVENTION

EphA2 is expressed differently in normal and metastatic cells. In normal breast and prostate epithelial cells, EphA2 is enriched in within sites of cell adhesion. Conversely, in metastatic prostate cells EphA2 is diffusely distributed, and in metastatic breast cancer cells EphA2 is redistributed into the membrane ruffles EphA2 expression is also known to be altered in lung and colon malignancies, and it is believed that EphA2 altered expression occurs in other types of metastases, particularly epithelial malignancies. Thus, techniques designed to alter EphA2 expression can be exploited to diagnose and treat metastatic disease.

In a preferred embodiment, antibodies specific for tyrosine phosphorylated proteins in cancer cells have been isolated and used to target cancer cells in passive immunotherapy. This approach is based upon the fact that many tyrosine kinases, e.g. Her2/Neu, are expressed by oncogenes and are therefore overexpressed in cancer cells. The present invention is directed to the production and use of antibodies capable of recognition of and specific binding to extracellular epitopes of the tyrosine kinase EphA2. The antibodies are produced by selected hybridomas, themselves the product of fusion of myeloma cells with lymph node cells harvested from animals subjected to a specific inoculation protocol designed for increased sensitivity and diversity of responding hybridomas.

Figure 1:
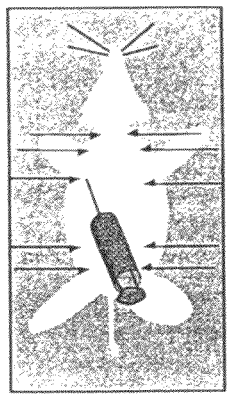
FIG. 1 is an overview of the RIMMS procedure, through which the antibodies of this invention are generated.

To produce these hybridomas, tyrosine phosphorylated proteins from Ras-transformed human epithelial cells were isolated by affinity chromatography using existing phosphotyrosine specific antibodies. The tyrosine phosphorylated proteins are then used as an immunogen for producing monoclonal antibodies according to the procedure illustrated in FIG. 1. Low-dose amounts of tyrosine phosphorylated proteins are injected proximal to lymph nodes of a mammal, every other day, over a ten day period (the RIMMS strategy). B cells from engorged lymph nodes are then isolated and fused with Bcl-2-overexpressing myeloma cells, to minimize apoptosis after fusion. This method results in increased diversity, specificity, and cost-effectiveness of hybridoma production. The hybridomas are screened to identify those hybridomas producing antibodies that distinguish malignant from normal cancer cells.

Hybridomas producing antibodies specific to EphA2 have been selected. Use of the RIMMS technique has resulted in the production of a multiplicity of hybridomas producing monoclonal antibodies that specifically bind EphA2. To date, at least 450 hybridomas have been identified which produce antibodies capable of distinguishing malignant from normal cancer cells. Of the first four such hybridomas to be characterized, two recognize independent epitopes on EphA2. The first, D7, produces an antibody recognizing an intracellular epitope. The second, B2D6, produces an antibody that specifically binds an extracellular epitope of EphA2, a characteristic that enables its effective use for the diagnosis and treatment of selected metastatic tumors. Murine hybridomas B2D6 and D7 were deposited on Dec. 8, 2000, with the American Type Culture Collection, 10801 University Boulevard, Manassas, Va. 20110-2209, and assigned ATCC Numbers PTA-2754 and PTA-2755, respectively.

While the RIMMS strategy has proven to be valuable in the production of EphA2 specific antibodies, other techniques are known in the art for producing antibodies to a specific antigen, and these techniques are within the scope of this invention.

It is known in the art to use antibodies to detect the presence or overexpression of a specific protein. Because EphA2 is overexpressed in metastatic cells, EphA2-specific antibodies of this invention may be used to detect this overexpression and, thus, to detect metastatic disease. Such techniques include but are not limited to western blotting, precipitation, agglutination, and ELISA assays. These techniques are well known in the art. Also, the extracellular epitope specificity of EphA2-specific antibodies of this invention can be exploited to detect changes in EphA2 localization which are associated with metastasis. In normal breast and prostate epithelial cells, EphA2 is enriched in within sites of cell adhesion, whereas in metastatic cells, EphA2 distribution is altered. In metastatic prostate cells EphA2 is diffusely distributed, and in metastatic breast cancer cells EphA2 is redistributed into the membrane ruffles. EphA2 expression is also known to be altered in lung and colon malignancies, and it is believed that EphA2 altered expression occurs in other types of metastasis, particularly epithelial malignancies Techniques such as immunohistological staining or immunofluorescent microscopy are well known in the art and may be used to visualize EphA2 distribution. See, for example, U.S. Pat. No. 5,514,554, hereby incorporated by reference. In order to detect overexpression or altered distribution of EphA2, the EphA2-specific antibodies may be labeled covalently or non-covalently with any of a number of known detectable labels, such as fluorescent or radioactive substances, as is known in the art. Alternatively, a secondary antibody specific for the antibodies of this invention is labeled with a known detectable label and used to detect the EphA2-specific antibodies in the above techniques. Thus, the antibodies of this invention provide methods to detect metastatic transformation.

The present invention also employs antibodies specific for an extracellular epitope of EphA2 in therapeutic compositions and methods for use.

When used for in vivo therapy, a pharmaceutical composition administered to a patient comprises EphA2-specific antibodies in therapeutically effective amounts in a pharmaceutically acceptable carrier. In a preferred embodiment, the EphA2-specific antibodies have been "humanized." Humanized antibodies include "chimeric antibodies" made by splicing genes from a mouse (or other mammal) antibody of appropriate antigen specificity together with genes from a human antibody molecule of appropriate biological activity. Such techniques are known in the art. See, for example, U.S. Pat. No. 5,811,098, hereby incorporated by reference. In addition to antibodies, natural or artificial ligands, peptides, anti-sense, ATP analogues, or other small molecules capable of specifically targeting EphA2 may be employed.

An example of another way to target EphA2 is the use of ephrins to activate or inhibit EphA2. For example, EphrinA1-$F_c$, the extracellular domain of ephrinA1 linked to immunoglobulin heavy chain, increases the phosphotyrosine content of EphA2. EphrinA1-$F_c$ reverses the malignant behavior of EphA2 transformed cells. Thus, another preferred embodiment of this invention is a pharmaceutical composition comprising an ephrin or a hybrid form of ephrin administered in a therapeutic amount.

Therapeutic amounts are amounts which eliminate or reduce the patient's tumor burden, or which prevent or reduce the proliferation of metastatic cells. The dosage will depend on many parameters, including the nature of the tumor, patient history, patient condition, the possible co-use of other oncolytic agents, and methods of administration. Methods of administration include injection (e.g., parenteral, subcutaneous, intravenous, intraperitoneal, etc.) for which the antibodies are provided in a nontoxic pharmaceutically acceptable carrier such as water, saline, Ringer's solution, dextrose solution, 5% human serum albumin, fixed oils, ethyl oleate, or liposomes. Typical dosages may range from about 0.01 to about 20 mg/kg, and more particularly from about 0.1 to about 10 mg/kg. Other methods of administration include oral and transdermal. Acceptable carriers for oral ingestion in accordance with the present invention can be formulated using art-recognized techniques into pharmaceutically acceptable liquid carriers or in combination with pharmaceutically acceptable solid carriers in the form of tablets, capsules, caplets, or gel-seals. Other effective methods of administration and dosages may be determined by routine experimentation and are within the scope of this invention.

Therapeutic methods employing EphA2-specific antibodies may be combined with chemotherapy, surgery, and radiation therapy, depending on type of the tumor, patient condition, other health issues, and a variety of factors. The methods may also include immunoconjugates for targeted immunotoxin-mediated therapy, wherein antibodies of this invention are covalently or non-covalently conjugated to various cytotoxic agents, further enhancing toxicity to targeted cells. See, for example, U.S. Pat. No. 5,872,223, hereby incorporated by reference. Such agents, including various bacterial toxins (e.g., Pseudomonas exotoxin), ricin A-chain, daunorubicin, methotrexate, and ribosome inhibitors (e.g., trichosantin). Also, the antibodies of this invention may be labeled with alpha, beta, or Auger electron emitters, resulting in immunoconjugates for targeted radiotherapy.

Thus, EphA2-specific antibodies may be used in a variety of methods and compositions for detecting and treating metastatic disease.

Example 1

Characterization of EphA2 Expression in Metastatic Cells

Following the RIMMS strategy using tyrosine phosphorylated proteins from Ras-transformed human epithelial cells, hybridomas were screened, and an antibody specific for EphA2 has been isolated. This antibody, B2D6, was used to assess the levels of EphA2 expression in nontransformed prostatic epithelial cells and prostatic tumor cells. Low levels of EphA2 expression were found in non-transformed prostatic epithelial cells, but this EphA2 expression was enriched within sites of cell-cell contact and interacted with cell-bound ligand. Compared to non-transformed cells, two features distinguish EphA2 in metastatic prostate cancer cells: 1) EphA2 is overexpressed; 2) EphA2 is diffusely distributed and does not appear to interact with ligand. To confirm these data, western blots were performed using the EphA2 specific antibodies. EphA2 overexpression in human prostate cancer cells (LNCAP, DU145, PC3) directly correlates with their invasiveness in vitro and in vivo.

Figures 2A, 2B, 2C:
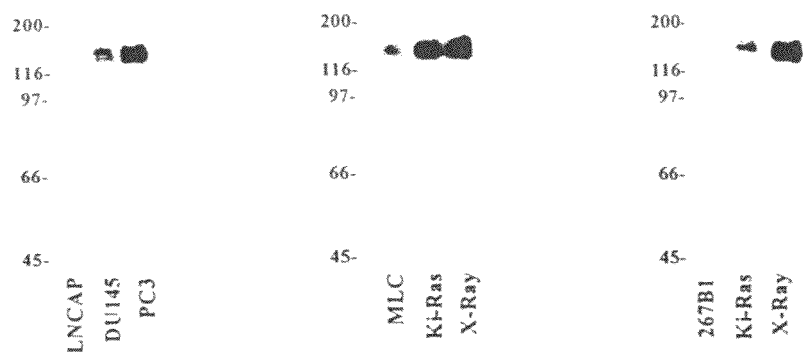
FIG. 2A-C show a series of western blots showing EphA2 expression in human cell lines.
Figure 3:
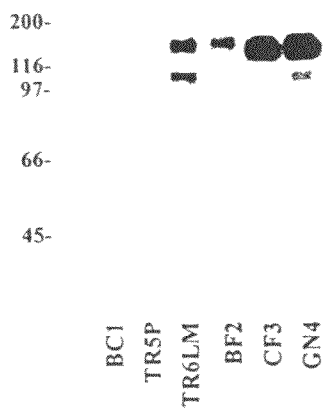
FIG. 3 is similar to FIG. 2, except showing EphA2 expression in canine prostatic cancer cells.

Of the three lines tested, LNCAP is the least aggressive, DU145 is more aggressive, and PC3 is the most aggressive. As seen in FIG. 2, DU145 cells exhibit higher levels of EphA2 expression than LNCAP, and PC3 cells exhibit even higher levels of EphA2 expression. Similarly, as shown in FIGS. 2B and 2C, EphA2 expression is elevated in variants of human prostatic epithelial cells transformed by oncogenic K-Ras or X-irradiation. The three lanes in FIG. 2B show "normal" MCL prostatic epithelial cells, and K-Ras and X-ray transformed cell lines derived therefrom. Similarly, the three lanes of FIG. 2C show "normal" 267B1 prostatic epithelial cells, and K-Ras and X-ray transformed cell lines derived therefrom. As seen in FIGS. 2B and 2C, the transformed cells all exhibited elevated EphA2 levels. FIG. 3 shows similar western blots, except using prostate cancer cell lines from dogs. As shown in FIG. 3, consistent with the results from human cells, EphA2 is overexpressed in metastatic prostatic carcinoma cells derived from dogs with spontaneous prostate cancer.

The metastatic prostate cell lines can be subdivided into three categories: 1) cells derived from primary prostate tumors; 2) cells derived from metastases that are poorly metastatic in vivo; 3) cells derived from metastases that are highly metastatic in vivo. The western blots using EphA2-specific antibodies have revealed that EphA2 expression is elevated in all cells derived from metastases, with highest EphA2 expression in cells that retain metastatic potential in vivo (as assessed using athymic mouse models). Interestingly, B2D6 studies have shown that EphA2 is overexpressed in cells from prostate cancer metastases compared to lines established from the primary tumor of same patient. Taken together, these results all reveal EphA2 overexpression in metastatic prostate tumor cells.

Similar EphA2 expression patterns have been found with breast cancer cells. In normal mammary epithelial cells, EphA2 is enriched within the cell-cell junctions. By contrast, non-metastatic breast cancer cells do not express EphA2, while metastatic breast cancer cells overexpress EphA2. In metastatic breast cancer cells, EphA2 is redistributed into the membrane ruffles and, thus, is available for antibody binding.

Example 2

In Vitro Targeting of Metastatic Cells

EphA2 overexpression renders metastatic cells susceptible to antibody-mediated selected killing with the present antibodies specific for an extracellular epitope of EphA2. While normal cells express EphA2, it is believed that ligand binding or clustering within sites of cell-cell contact occludes extracellular epitopes in normal cells and renders them inaccessible to antibodies specific for an extracellular epitope of EphA2. The tumor selectivity of the antibodies of the present invention is believed to rival or exceed that of Herceptin® for targeting metastatic cancer.

EphA2 overexpression provides a basis for targeting metastatic cancer cells with EphA2-specific antibodies. Antibodies specific for an extracellular epitope of EphA2, such as those produced by hybridoma B2D6, may be used to alter selectively (versus normal cells) the proliferative or invasive behaviors of metastatic cancer cells. In both metastasis-derived and laboratory-induced transformation, EphA2 overexpression correlates with invasiveness, whereas non-invasive cells have lower levels of EphA2 expression.

To measure the effect of B2D6 on cell growth, cells are incubated with purified B2D6, and cell proliferation is measured by counting cells microscopically (using a hemacytometer) and by measuring DNA synthesis. For example, normal growth media is supplemented with B2D6 and BrdU, and BrdU incorporation is measured over the following four hours. To measure the effects of B2D6 over longer times, samples are counted at 24 hour intervals, with BrdU added to the culture media for the final four hours of incubation. As a third measure of cell growth, the effect of B2D6 on the growth of metastatic cells in soft agar is determined. Soft agar plating assays are used, wherein $2 \times 10^4$ metastatic cells are plated atop agar, in the presence or absence of B2D6 (0-10 nM), and colony growth is evaluated at three-day intervals thereafter.

It is believed that B2D6 decreases the growth of metastatic cells. Preliminary results reveal that B2D6 aggregates EphA2 and blocks about 50% of growth of metastatic breast cancer cells (which also overexpress EphA2) over the first four hours of incubation. Although EphA2 is not tyrosine phosphorylated in metastatic breast cancer cells, tyrosine phosphorylation is restored in these B2D6 treated cells. Thus, B2D6 is believed to restore normal EphA2 function.

Additional studies with prostate cancer cells are being performed to determine if longer incubations with B2D6 further inhibit metastatic cell growth. Non-transformed epithelial cells express some EphA2, albeit much less than metastatic cells, and some toxicity to non-transformed cells is possible. The minimum effective and maximum non-toxic dosage levels of antibodies in accordance with one aspect of this invention can be identified by routine experimentation, but preferably, typical doses will range from about 0.1 to about 20 mg/kg of patient body weight. The preferred dose will depend on many parameters, including the nature of the tumor, patient history, patient condition, the possible co-use of other oncolytic agents, and methods of administration. Antibody levels that best discriminate between normal and metastatic cells will be used in treatment of metastatic tumors overexpressing EphA2 proteins.

Example 3

In Vitro Antibody Mediated Cytotoxicity

Preliminary results demonstrate that EphA2 antibodies impede metastatic cell growth. To measure antibody-directed cytotoxicity, preferably, non-radioactive versions of $^{51}$Cr-release assays using target cells (normal or metastatic prostatic epithelial cells) labeled with europium chloride ($EuCl_3$) and diethylenetriamine-pentaacetic acid (DTPA) are performed. After washing away unincorporated $Eu^{3+}$, naphthoyltrifluoroacetone (NTA) and trioctylphosphine oxide are incubated with the cytolytic agents and assay supernatants. The luminescence of resultant ternary complex ($Eu^{3+}$/NTA/trioctylphosphine oxide) is measured using a fluorescence microplate reader. The sensitivity of this $Eu^{3+}$-release assay for complement-mediated cytolysis has been reported to be five-fold better than $^{51}$Cr-release assays. To determine specific lysis, parallel samples are hyponically lysed by adding distilled water. Untreated samples and isotype matched antibodies serve as negative controls.

To model complement-mediated death in vitro, cells are labeled with B2D6 and exposed to sera that has not been heat-inactivated. For antibody dependent cellular cytotoxicity ("ADCC"), both control and B2D6-treated prostate cells are incubated with peripheral blood mononuclear cells (PBMC; 10:1 E/T ratio).

It is believed that complement and ADCC both promote specific killing of the metastases. Antibody dose can be varied in order to establish $LD_{50}$ measurements for metastatic and normal cells. Antibody concentrations that maximize specific killing of metastatic cells (PC3, 267-Ras, 267-X) while minimizing the death to non-transformed prostatic epithelia (267, MLC) are determined by routine experimentation. Also, ADCC can be combined with complement to further enhance tumor killing by treating the samples with tumor necrosis factor (TNF). There is evidence that TNF potentiates the killing of tumor cells by EGFR and Her2-specific antibodies. It is expected that humanizing the antibodies of this invention would provide for better complement or ADCC results.

It is believed that B2D6 kills tumor cells through complement cascade or ADCC. However, covalent or non-covalent conjugation of the present antibodies to art-recognized cytotoxic agents can further enhance toxicity to targeted cells. Examples of toxins appropriate for immunoconjugation include Pseudomonas exotoxin or ricin A-chain.

Example 4

In Vivo targeting of Metastatic Cells

The present EphA2 antibodies, particularly those produced by hybridoma B2D6, are effective in blocking the growth and invasiveness of prostate cancer cells in vivo. The efficacy of B2D6 in blocking the growth of primary prostate tumors using subcutaneous implantation of PC3 tumor cells in mice is determined by use of subcutaneous models. The primary advantages of subcutaneous models are the ease of implantation and subsequent monitoring of tumor size. $5 \times 10^5$ PC3 cells are inoculated subcutaneously into the right craniolateral thorax (axilla) using aseptic technique. Tumors are measured every 3-4 days using vernier calipers until they reach a volume of 0.2-0.3 cm$^3$. At that time, the mice are divided into four groups (8-10 animals each): Group 1 (vehicle control), Groups 2-4 are treated with 0.1, 1.0, or 10 mg/kg B2D6, administered intraperitoneally, twice a week. The mice are then monitored every 3 days to measure tumor volume (with vernier calipers), body weight, and life span. After no greater than 60 days past implantation, the animals are sacrificed and postmortem evaluations of tumorigenesis, including measurement and weight of implanted tumors and proximal lymph nodes, macroscopic evaluation of soft tissues for tumors (lymph nodes and lung), and formalin fixation of the primary tumor and tissues, are performed. The tissues are evaluated by immunohistochemistry using D7 (another EphA2 specific antibody that is amenable to immunohistochemistry) to determine the level of EphA2 expression in the tumors. In particular, tumor cells that escape B2D6 treatment are studied to determine whether they have low levels of EphA2 expression. Also, EphA2 expression in the individual animals is correlated with tumor invasiveness.

As target-negative controls for specificity, parallel studies are performed using DU145 cells, which express very low levels of EphA2. Whereas the growth of PC3 tumors are believed to be sensitive to B2D6, tumors caused by DU145 are believed be insensitive. Statistical significance of B2D6 inhibition of tumorigenicity, overall metastatic frequency, and frequency of distant metastases is tested using computerized statistical packages (PC/SAS Ver. 6.04), with differences considered significant if $p<0.05$.

While subcutaneous implantation is a popular and valuable method for modeling tumor cell growth, differences between the microenvironment of the skin and prostate can cause rather dramatic differences in cell behavior. For example, PC3 cells rarely metastasize when implanted subcutaneously whereas intraprostatic implantation (orthotopic) facilitates metastasis. Thus, PC3 cells are implanted in the prostate by exposing the prostate via laparotomy and inoculating tumor cells into prostate gland using a surgical microscope. After seven days, the mice begin receiving treatment with B2D6, as described above, and the animals are sacrificed no later than 60 days after implantation (or if the animals become moribund). The tumors are palpated at 3-5 day intervals, at which time data on tumor size, animal weight, and survival are collected. Post-mortem evaluations are also performed as described above, with emphasis upon the effect of B2D6 upon metastatic potential (to lungs and regional lymph nodes). B2D6 is believed to block the primary tumor and metastatic potential of PC3 cells in a dose-dependent manner.

To minimize identification of strain or clonal-specific effects, identical analyses using other model systems can be employed. For example, the effects of B2D6 on the growth or metastasis of tumors caused by implantation of K-Ras or X-ray transformed 267B 1 can be compared to the effects on MLC human prostatic epithelial cell lines.

Example 5

Development of "Second Generation" EphA2-based Antibody Therapeutics

While EphA2 overexpression in metastatic prostate cancer cells provides a degree of selectivity comparable to Herceptin® in breast cancer, unique properties of EphA2 are believed to allow for even more selective targeting. In particular, EphA2 at the surface of non-transformed epithelia is tightly packed into cell-cell contacts whereas EphA2 on metastatic cells is diffusely distributed. It is thus likely that some epitopes on EphA2 are accessible in metastases but protected by ligand in normal prostatic epithelia. The EphA2 antibodies that provide the optimal discrimination between normal and metastatic prostatic epithelia are selected.

Figure 4:
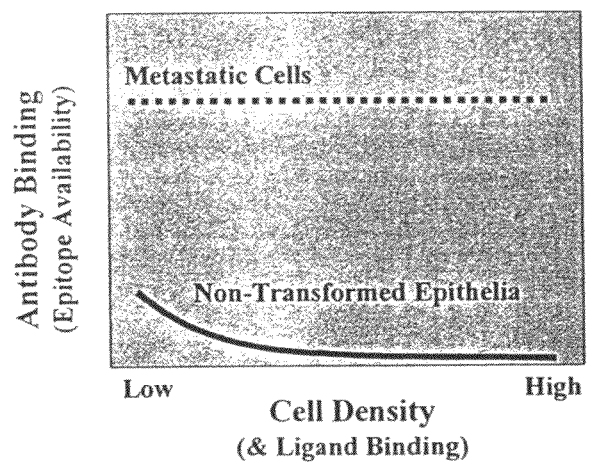
FIG. 4 shows predicted antibody binding plotted against cell density in a screening procedure for antibodies which are specific for an extracellular epitope of EphA2.

The panel of antibodies generated previously are screened for epitopes on EphA2 that are found at the cell surface. Using flow cytometry, EphA2 expression in a variety of "normal" (e.g., 267B or MLC cells) and metastatic cells (PC3 cells) are compared. For example, confluent monolayers of normal and metastatic cells are labeled with B2D6. To insure that antibodies are selected that are specific for epitopes inaccessible in normal cells but accessible in metastatic cells, antibodies are selected whose binding decreases in normal cells with increasing cell density but whose binding remains constant in metastatic cells, as shown in FIG. 4. After labeling with fluorescein-secondary antibodies, EphA2 expression is evaluated by using flow cytometry. The antibodies that best distinguish between normal and metastatic cells are selected. Specificity for EphA2 is confirmed via western blotting and immunoprecipitation studies. Antibodies exhibiting the best selectivity are then humanized using art recognized techniques.

Example 6

Altered EphA2 Expression Through Transfection

To assess the consequences of EphA2 overexpression, MCF-10A cells were transfected with human EphA2 cDNA (EphA2) or a vector control (vector). After establishing cultures of MCF-10A cells with stable overexpression of EphA2, microscopic evaluation revealed differences in the cell morphology as compared to vector-transfected control cells (not shown). Non-transformed MCF-10A cells display an epithelial morphology and interact with one-another, even at low cell density. In contrast, EphA2-overexpressing MCF-10A cells (MCF$^{EphA2}$) adopt a fibroblast-like morphology and do not form cell-cell contacts, even at high cell density. To confirm that the mesenchymal morphology does not represent clonal variation, a separate sample of MCF-10A cells transfected with EphA2 cDNAs yielded identical results.

Cell-ECM adhesions were evaluated by incubating cells on ECM at 37° C. for 30 minutes before vigorous washing to remove weakly adherent cells. These assays revealed a 24-fold increase in ECM attachments in MCF$^{EPhA2}$ cells relative to vector-transfected controls ($P<4\times10^{-4}$). Cell-cell adhesions were assayed by incubating cells in suspension and counting the average size of cell colonies. Whereas vector-transfected MCF-10A cells interact with one-another in colonies with an average size of 4.1 cells, the average colony size of MCF$^{EPhA2}$ cells is reduced to 1.3 cells ($P<3\times10^{-5}$).

Since stable cell-cell contacts cause EphA2 to become enriched within sites of cell-cell contact, EphA2 subcellular localization was assessed by immunostaining with specific antibodies. The EphA2 on non-transformed MCF-10A cells was restricted to a narrow line where adjacent cells came into direct contact, with little staining of membrane that was not in contact with neighboring cells. In contrast, the pattern of EphA2 staining on MCP$^{EphA2}$ cells was diffuse, with little staining of cell-cell contacts.

The lack of EphA2 within cell-cell contacts in MCF$^{EPhA2}$ cells was intriguing since EphA2 is stimulated by ligands that are anchored to the cell membrane. To measure EphA2 stimulation, the phosphotyrosine content of immunoprecipitated EphA2 was measured by Western blot analysis with phosphotyrosine specific antibodies. Whereas the EphA2 in vector-transfected MCF-10 cells was tyrosine phosphorylated, EphA2 was not tyrosine phosphorylated in MCF$^{EPhA2}$ cells. The decreased phosphotyrosine content was confirmed using multiple EphA2 antibodies for immunoprecipitation (D7, B2D6) and different phosphotyrosine-specific antibodies (4G10, PY20) for Western blot analyses.

Example 7

Malignancy and Metastasis Through EphA2 Transfection

Malignant transformation was studied in vitro, and MCF$^{EPhA2}$ cells were found to colonize soft agar. Whereas vector-transfected MCF-10A cells formed 0.3 colonies per high-power field, while MCF$^{EPhA2}$ cells displayed increased colony growth in soft agar, with an average of 3.0 colonies per high-power field (P<$3 \times 10^{-7}$). Vector and EphA2 overexpressing MCF-10A cells were allowed to interact with Matrigel (Collaborative, Bedford, Mass.). Non-transformed MCF-10A cells rapidly organized into spherical colonies when cultured on Matrigel whereas MCF$^{EPhA2}$ cells adopted a stellate organization that was indistinguishable from the behavior of metastatic cells (e.g., MDA-MB-231, MDA-MB,435).

Since in vitro analyses of transformation do not always predict tumorigenic potential in vivo, control or EphA2-overexpressing MCF-10A cells were implanted into athymic (nu/nu) mice. Subcutaneous injection of MCF$^{EPhA2}$ cells caused the formation of palpable tumors within four days in 19 of 19 mice. The median volume of resulting tumors related to the number of implanted cells and reached an average of 300 mm$^3$ (for samples injected with $5 \times 10^6$ cells) within 10 days (Table I). Necropsy revealed that the tumors were firmly attached to the underlying axillary muscle and surrounded by fibrous tissue. Histologically, the neoplastic cells were invasive and associated with fibrous connective tissue. These neoplastic cells exhibited moderate cytoplasmic and nuclear pleiomorphism and formed dysplastic tubular and secreting structures. In control experiments, cells transfected with vector DNA failed to grow in athymic mice (0 of 13; Table I) and necropsy failed to identify any growth or invasion of these cells.

Since the highest levels of EphA2 were consistently found in breast cancer cells that are metastatic in vivo, $1 \times 10^6$ control or MCF$^{EPhA2}$ cells were injected into the tail vein of athymic mice. Within seven days, necropsy revealed lung micrometastases within large vessels in 2 of 4 mice injected with MCF$^{EPhA2}$ cells (Table I). The metastases were generally found to occlude large blood vessels but did not breach the vessel wall. Immunohistochemical staining with cytokeratin antibodies confirmed the epithelial nature of the thrombus and a lack of anti-thrombin staining revealed that the thrombus did not represent an abnormal or atypical outgrowth of endothelial cells. No lung colonization was observed in mice that had been injected with control MCF-10A cells (Table I).

TABLE I

Tumorigenic and Metastatic Potential of EphA2-Transformed MCF-10A Cells

| Cell | Site of Inoculation | # of Cells Injected | Incidence of Tumorigenicity | Tumor Volume (mm$^3$) |
|---|---|---|---|---|
| Ctrl | Subcutaneous | $1 \times 10^6$ | 0/9 | N/A |
| EphA2 | | $1 \times 10^6$ | 9/9 | 66 ± 20 |
| Ctrl | Subcutaneous | $5 \times 10^6$ | 0/4 | N/A |
| EphA2 | | $5 \times 10^6$ | 10/10 | 293 ± 70 |
| Ctrl | Tail Vein | $1 \times 10^6$ | 0/4 | |
| EphA2 | | $1 \times 10^6$ | 2/4 | |

Example 8

Metastatic Targeting Using EphA2 Agonists

To test if EphA2 could be stimulated by an agonist, MCF$^{EPhA2}$ cells were suspended in soft agar in the presence or absence of 0.5 mg/mL EphrinA1-F$_c$. EphrinA1-F$_c$ increased the phosphotyrosine content of EphA2, and EphrinA1-F$_c$-treated cells exhibited reduced colony formation in soft agar by 49% relative to vehicle-treated controls (P<$5 \times 10^{-6}$). To test if EphA2 stimulation could alter cell behavior on Matrigel, the MCF$^{EPhA2}$ cells were treated with 0.5 mg/mL EphrinA1-F$_c$, which restored a spherical phenotype that was comparable to non-transformed MCF-10A cells. Thus, EphA2 stimulation reverses the effects of EphA2 overexpression. Despite its inability to interact with its endogenous ligands, the EphA2 in MCF$^{EPhA2}$ cells responded to exogenous stimuli.

Although the invention has been described in detail with reference to preferred embodiments, variations and modifications exist within the scope and spirit of the invention as described and defined in the following claims.

What is claimed is:

1. A method for treatment of a patient having a tumor comprising cells that express EphA2, said method comprising administering to the patient the extracellular domain of ephrinA1 linked to Fc, or an anti-EphA2 antibody that interacts with an extracellular portion of EphA2 and increases tyrosine phosphorylation of EphA2, in an amount effective to reduce or inhibit the growth, proliferation, or invasiveness of the tumor.

2. The method of claim 1 wherein the tumor comprises a primary tumor.

3. The method of claim 1 wherein the tumor comprises a metastatic tumor.

4. The method of claim 1 wherein the tumor has metastatic potential.

5. The method of claim 1 wherein the tumor comprises a breast cancer cell.

6. The method of claim 1 wherein the anti-EphA2 antibody is a monoclonal antibody.

* * * * *